United States Patent
Amirouche et al.

(10) Patent No.: US 10,130,759 B2
(45) Date of Patent: *Nov. 20, 2018

(54) MULTI-PORTED DRUG DELIVERY DEVICE HAVING MULTI-RESERVOIR CARTRIDGE SYSTEM

(75) Inventors: Farid Amirouche, Highland Park, IL (US); Matthew L. Cantwell, Northbrook, IL (US)

(73) Assignee: PICOLIFE TECHNOLOGIES, LLC, Jacksonville, FL (US)

( * ) Notice: Subject to any disclaimer, the term of this patent is extended or adjusted under 35 U.S.C. 154(b) by 727 days.

This patent is subject to a terminal disclaimer.

(21) Appl. No.: 13/416,249

(22) Filed: Mar. 9, 2012

(65) Prior Publication Data
US 2013/0237947 A1   Sep. 12, 2013

(51) Int. Cl.
*A61M 5/145* (2006.01)
*A61M 5/148* (2006.01)

(52) U.S. Cl.
CPC ........ *A61M 5/14586* (2013.01); *A61M 5/148* (2013.01); *A61M 2205/12* (2013.01); *A61M 2205/502* (2013.01)

(58) Field of Classification Search
CPC .............. A61M 5/14586; A61M 5/148; A61M 2205/502; A61M 2205/12
See application file for complete search history.

(56) References Cited

U.S. PATENT DOCUMENTS

| 2,398,435 A | 4/1946 | Marks |
|---|---|---|
| 3,137,242 A | 6/1964 | Hahn |
| 3,498,228 A | 3/1970 | Blumie et al. |
| 3,691,263 A | 9/1972 | Stoy et al. |
| 3,771,694 A | 11/1973 | Kaminski |
| 3,827,565 A | 8/1974 | Matsumura |
| 3,889,710 A | 6/1975 | Brost |

(Continued)

FOREIGN PATENT DOCUMENTS

| EP | 0 024 431 B1 | 8/1985 |
|---|---|---|
| EP | 0 299 628 A1 | 1/1989 |

(Continued)

OTHER PUBLICATIONS

"Bartels micropumps," Apr. 2009, [online] http://www.bartelsmikrotechnik.de/index.php/micropumps.html.

(Continued)

*Primary Examiner* — Bhisma Mehta
*Assistant Examiner* — Hamza Darb
(74) *Attorney, Agent, or Firm* — Ashkan Najafi

(57) ABSTRACT

A cartridge system of a multi-ported drug delivery device with independently actuated collapsible reservoirs, for delivery of medicaments, which includes membranes placed between disk magnets that are housed within pump body inserts. The pump body inserts having flow channels and fluid openings are between two inlet/outlet members with communication control through active valves and dynamically stressed membranes. The inlet/outlet members of the cartridge system each having a fluid outlet component and fluid openings are securely engaged to two or more reservoirs containing fluid medicaments. The cartridge system driven by the pump driver system delivers an appropriate dosage of medicament for treatment prescribed.

9 Claims, 61 Drawing Sheets

(56) References Cited

U.S. PATENT DOCUMENTS

| | | |
|---|---|---|
| 3,915,609 A | 10/1975 | Robinson |
| 4,017,238 A | 4/1977 | Robinson |
| 4,197,266 A | 4/1980 | Clark et al. |
| 4,257,416 A | 3/1981 | Prager |
| 4,340,048 A | 7/1982 | Eckenhoff |
| 4,376,618 A | 3/1983 | Toyoda et al. |
| 4,415,003 A | 11/1983 | Paradis et al. |
| 4,498,843 A | 2/1985 | Schneider et al. |
| 4,544,369 A | 10/1985 | Skakoon et al. |
| 4,552,561 A | 11/1985 | Eckenhoff et al. |
| 4,657,486 A | 4/1987 | Stempfle et al. |
| 4,712,583 A | 12/1987 | Pelmulder et al. |
| 4,731,726 A | 3/1988 | Allen, III |
| 4,784,644 A | 11/1988 | Sawyer et al. |
| 4,797,144 A | 1/1989 | DeMeritt et al. |
| 4,840,754 A | 6/1989 | Brown et al. |
| 4,936,833 A | 6/1990 | Sams |
| 4,938,742 A | 7/1990 | Smits |
| 4,946,448 A | 8/1990 | Richmond |
| 4,947,856 A | 8/1990 | Beard |
| 4,958,661 A | 9/1990 | Holtermann et al. |
| 4,966,199 A | 10/1990 | Ruschke |
| 5,019,974 A | 5/1991 | Beckers |
| 5,050,612 A | 9/1991 | Matsumura |
| 5,147,523 A | 9/1992 | Yagawara et al. |
| 5,218,993 A | 6/1993 | Steinberg et al. |
| 5,246,634 A | 9/1993 | Ichikawa et al. |
| 5,370,635 A | 12/1994 | Strausak et al. |
| 5,584,815 A | 12/1996 | Pawelka et al. |
| 5,645,855 A | 7/1997 | Lorenz |
| 5,674,557 A | 10/1997 | Widman et al. |
| 5,709,662 A | 1/1998 | Olive et al. |
| 5,762,632 A | 6/1998 | Whisson |
| 5,775,671 A | 7/1998 | Cote, Sr. |
| 5,822,715 A | 10/1998 | Worthington et al. |
| 5,858,001 A | 1/1999 | Tsals et al. |
| 6,003,736 A | 12/1999 | Ljunggren |
| 6,017,331 A | 1/2000 | Watts et al. |
| 6,056,718 A | 5/2000 | Funderburk et al. |
| 6,305,661 B1 | 10/2001 | Kennedy |
| 6,311,712 B1 | 11/2001 | Meyer |
| 6,315,929 B1 | 11/2001 | Ishihara et al. |
| 6,390,120 B1 | 5/2002 | Guala |
| 6,409,707 B1 | 6/2002 | Guala |
| 6,572,586 B1 | 6/2003 | Wojcik |
| 6,627,124 B1 | 9/2003 | Herbrechtsmeier et al. |
| 6,648,859 B2 | 11/2003 | Bitdinger et al. |
| 6,723,086 B2 | 4/2004 | Bassuk et al. |
| 6,813,906 B1 | 11/2004 | Hirota et al. |
| 6,945,963 B2 | 9/2005 | Langley et al. |
| 7,044,125 B2 | 5/2006 | Vedrine et al. |
| 7,081,108 B2 | 7/2006 | Langley et al. |
| 7,104,973 B2 | 9/2006 | Woolston et al. |
| 7,123,985 B2 | 10/2006 | Wildsmith et al. |
| 7,296,782 B2 | 11/2007 | Enerson et al. |
| 7,302,311 B2 | 11/2007 | Varis |
| 7,407,490 B2 | 8/2008 | Bendsen et al. |
| 7,470,266 B2 | 12/2008 | Massengale et al. |
| 7,510,544 B2 | 3/2009 | Vilks et al. |
| 7,537,590 B2 | 5/2009 | Santini, Jr. et al. |
| 7,585,167 B2 | 9/2009 | Lawton et al. |
| 7,637,899 B2 | 12/2009 | Woolston et al. |
| 7,846,146 B2 | 12/2010 | Woolston et al. |
| 7,850,663 B2 | 12/2010 | Sullivan et al. |
| 7,896,002 B2 | 3/2011 | Watanabe |
| 7,914,499 B2 | 3/2011 | Gonnelli et al. |
| 7,935,280 B2 | 5/2011 | Lawton et al. |
| 7,967,795 B1 | 6/2011 | Cabiri |
| 8,021,334 B2 | 9/2011 | Shekalim |
| 8,771,229 B2 | 7/2014 | Amirouche et al. |
| 2002/0119711 A1 | 8/2002 | VanAntwerp et al. |
| 2003/0100883 A1 | 5/2003 | Kristensen et al. |
| 2003/0180164 A1 | 9/2003 | Bunner et al. |
| 2004/0050104 A1 | 3/2004 | Ghosh et al. |
| 2004/0176727 A1 | 9/2004 | Shekalim |
| 2005/0065500 A1 | 3/2005 | Couvillon, Jr. et al. |
| 2005/0192557 A1 | 9/2005 | Brauker et al. |
| 2006/0021386 A1 | 2/2006 | Wang |
| 2006/0073232 A1 | 4/2006 | Wang |
| 2006/0145372 A1 | 7/2006 | Jones et al. |
| 2006/0224109 A1 | 10/2006 | Steil et al. |
| 2007/0073230 A1 | 3/2007 | Jasperson et al. |
| 2007/0087068 A1 | 4/2007 | Eiha et al. |
| 2007/0225147 A1 | 9/2007 | Hayashi et al. |
| 2007/0233008 A1 | 10/2007 | Kristensen et al. |
| 2007/0299398 A1 | 12/2007 | Alferness et al. |
| 2008/0169444 A1 | 7/2008 | Guala |
| 2009/0062767 A1 | 3/2009 | Van Antwerp et al. |
| 2009/0069650 A1 | 3/2009 | Jennewine |
| 2009/0105658 A1 | 4/2009 | Jennewine |
| 2010/0004603 A1 | 1/2010 | Kristensen et al. |
| 2010/0081993 A1 | 4/2010 | O'Connor |
| 2010/0100077 A1 | 4/2010 | Rush et al. |
| 2010/0185322 A1 | 7/2010 | Bylsma et al. |
| 2010/0225013 A1 | 9/2010 | Eiha et al. |
| 2010/0241086 A1 | 9/2010 | Yodfat et al. |
| 2010/0255366 A1 | 10/2010 | Myland |
| 2010/0256593 A1 | 10/2010 | Yodfat et al. |
| 2010/0280461 A1 | 11/2010 | Forstreuter |
| 2010/0317093 A1 | 12/2010 | Turewicz et al. |
| 2011/0021905 A1 | 1/2011 | Patrick et al. |
| 2011/0066131 A1 | 3/2011 | Cabiri |
| 2011/0114744 A1 | 5/2011 | Ricciardi et al. |
| 2011/0118675 A1 | 5/2011 | Miller et al. |
| 2011/0137287 A1 | 6/2011 | Gonnelli et al. |
| 2011/0160696 A1 | 6/2011 | Hoss |
| 2011/0168294 A1 | 7/2011 | Jakobsen et al. |
| 2011/0251546 A1 | 10/2011 | Sullivan et al. |
| 2011/0274566 A1* | 11/2011 | Amirouche ....... A61M 5/14224 417/322 |
| 2011/0308650 A1 | 12/2011 | Amirouche et al. |
| 2011/0309229 A1 | 12/2011 | Amirouche et al. |
| 2011/0309552 A1 | 12/2011 | Amirouche et al. |
| 2012/0002422 A1 | 1/2012 | Lia et al. |
| 2012/0053571 A1 | 3/2012 | Petri |
| 2012/0330228 A1* | 12/2012 | Day ................. A61M 5/14244 604/82 |
| 2013/0144214 A1* | 6/2013 | Amirouche ......... A61M 5/1422 604/151 |
| 2013/0144254 A1 | 6/2013 | Amirouche et al. |
| 2013/0274576 A1 | 10/2013 | Amirouche et al. |
| 2013/0274577 A1 | 10/2013 | Amirouche et al. |
| 2013/0345650 A1 | 12/2013 | Amirouche |
| 2014/0155819 A1 | 6/2014 | Amirouche et al. |

FOREIGN PATENT DOCUMENTS

| | | |
|---|---|---|
| GB | 2 248 891 A | 4/1992 |
| JP | 62-297120 A | 12/1987 |
| JP | 2007-015906 A | 1/2007 |
| JP | 2007-0119280 A | 5/2007 |
| JP | 2008-96089 A | 4/2008 |
| WO | WO 03/047426 A1 | 6/2003 |
| WO | WO 2004/067964 A | 8/2004 |
| WO | WO 2006/111775 A | 10/2006 |
| WO | WO 2007/055642 A1 | 5/2007 |
| WO | WO 2009/048462 A1 | 4/2009 |
| WO | WO 2010/128914 A1 | 11/2010 |

OTHER PUBLICATIONS

"Diabetes Basics: Diabetes Statistics," American Diabetes Association, [Online]. Available at: http://www.diabetes.org/diabetes-basics/. [Accessed May 14, 2012] (3 pages).

"Diabetic Neuropathy, Living With Numbness and Pain," A Diabetic Life, [Online]. Available at: http://www.a-diabetic-life.com/diabetic-neuropathy.html. [Accessed May 5, 2012] (3 pages).

"Electromyogram (EMG)," MedicineNet.com, [Online]. Available at: http://www.medicine.net.com/electromyogram/article.htm. [Accessed May 15, 2012] (3 pages).

"Nerve conduction velocity." MedlinePlus®, A Service of the U.S. National Library of Medicine, National Institutes of Health, [Online].

(56) References Cited

OTHER PUBLICATIONS

Available at: http://www.nlm.nih.gov/medlineplus/ency/article/003927.htm; updated Jun. 18. 2011 (3 pages).
"Peripheral Neuropathy Fact Sheet." National institute of Neurological Disorders and Stroke, NIH Publication No. 04-4853, [Online]. Available: http://www.ninds.nih.gov/disorders/peripheralneuropathy/detail_peripheralneuropathy.htm; updated Sep. 19, 2012 (9 pages).
"Peripheral Neuropathy Market Approaches US$1B by 2012," PR Newswire, United Business Media [Online], Available at: http://www.prnewswire.co.uk/news-releases/peripheral-neuropathymarket-approaches-us1b-by-2012-154534705.html. Apr. 7, 2012 (2 pages).
"Silastic® BiaMedical Grade ETR elastomers", Dow Corning, 2002-2011, accessed at http://www4.dowcorning.com/DataFiles/090007c88028669a.pdf (5 pages).
"SILASTIC © Biomedical Grade Liquid Silicone Rubbers", Dow Corning, 2006, accessed at http://www4.dowcorning.com/DataFiles/090007c880097f96.pdf (6 pages).
"Small, powerful, light, precise: micro diaphragm pumps made of plastics: thinXXS micropumps" Mar. 2009, [online] http://www.thinxxs.com/main/produkte/micropumps.html (2 pages).
"Sylgard® 184 Silicone Elastomer", Dow Corning, 2007, accessed at http://ncnc.engineering.ucdavis.edu/pages/equipment/Sylgard_184_data_sheet.pdf (3 pages).
Acevedo, "Creation of Dual Chamber Micropump Using Rapid Prototyping," Milwaukee School of Engineering, Research Experience for Undergraduates Paper, 2005. Available online at: http://www.msoe.edu/academics/research_centers/reu/pdf/2005/Creation%20of%20a%20Dual%20Chamber%20Micropump%20using%20Rapid%20Prototyping.pdf (6 pages).
Amirouche et al., "Current Micropump Technologies and Their Biomedical Applications," Microsystem Technology, 2009, pp. 647-666, vol. 15.
Anhalt et al., "Insulin Patch Pumps; Their Development and Future in Closed-Loop Systems," *Diabetes Technology & Therapeutics*, 2010, pp. 51-58, vol. 12.
Bak et al., "Multiple Insulin Injections Using a Pen Injector Versus Insulin Pump Treatment in Young Diabetic Patients," Diabetes Research, 1987, pp. 155-158, vol. 6.
Barbano et al., "Effectiveness, Tolerability, and impact on Quality of Life of the 5% Lidocaine Patch in Diabetic Polyneuropathy," Archives of Neurology, 2004, pp. 914-918, vol. 61, No. 6.
Bohm et al., "A plastic rnicropump constructed with conventional techniques and materials," Sensors and Actuators A, vol. 77-3, pp. 223-228, 1999.
Casella et al., "Accuracy and Precision of Low-Dose Insulin Administration," Pediatrics. 1993, pp. 1155-1157, vol. 91.
Dario et al., "A fluid handling system for a chemical microanalyzer," J. Micromech. Microeng., vol. 6, pp. 95-98, 1996.
Davis et al., "Techniques for Improved Soft Lens Fitting"; Aug. 1, 2005, p. 2, accessed at http://www.clspectrum.com/articleviewer.aspx?articleid=12852 (5 pages).
Einhorn et al., "Advances in Diabetes for the Millennium: Insulin Treatment and Glucose Monitoring," Medscape General Medicine, 2004, p. 8, vol. 6, (3 Suppl.) [Online]. Available at: http://www.medscape.org/viewarticle/488996 (9 pages).
Elleri et al., "Closed-Loop Insulin Delivery for Treatment of Type 1 Diabetes," BMC Medical, 2011, p. 120, vol. 9 [Online]. Available at: http://www.biomedcentral.com/1741-7015/9/120 (9 pages).
Farnbach, "Peripheral Nerve Testing and Electromyography," [Online]. Available at: http://cal.vet.upenn.edu/projects/saortho/appendix_d/appd.htm. [Accessed May 18, 2012] (10 pages).
Fu et al, "TiNi-based thin films in MEMS applications: a review," Sensors and Actuators A, 2004, pp. 395-408, vol. 112, No. 23.
Galer et al., "The Lidocaine Patch 5% Effectively Treats All Neuropathic Pain Qualities: Results of a Randomized, Double-Blind, Vehicle-Controlled, 3-Week Efficacy Study with Use of the Neuropathic Pain Scale," The Clinical Journal of Pain, 2002, pp. 297-301, vol. 18, No. 5 (Abstract).
Gammaitoni et al., "Pharmacokinetics and Tolerability of Lidocaine Patch 5% with Extended Dosing," The Annals of Pharmacotherapy, 2002, pp. 236-240, vol. 36, No. 2, (Abstract).
Ha et al., "Disposable thermo-pneumatic micropump for bio lab-on-a-chip application," Microelectronic Engineering, 2009. pp. 1337-1339, vol. 86.
Ignaut et al., "Comparative Device Assessments: Humalog KwikPen Compared with Vial and Syringe and FlexPen," The Diabetes Educator, 2009, pp. 789-798, vol. 35, No. 2.
International Search Report and Written Opinion issued in International Patent Application No. PCT/US2009/059020, dated Mar. 9. 2010 (17 pages).
International Search Report and Written Opinion issued in International Patent Application No. PCT/US2012/066937, dated Mar. 7, 2013 (7 pages).
International Search Report and Written Opinion issued in International Patent Application No. PCT/US2013/035918, dated Jun. 21, 2013 (9 pages).
International Search Report and Written Opinion issued in International Patent Application No. PCT/US2013/035921, dated Jul. 1, 2013 (11 pages).
International Search Report and Written Opinion issued in International Patent Application No. PCT/US2013/046546, dated Aug. 8, 2013 (11 pages).
International Search Report and Written Opinion issued in International Patent Application No. PCT/US2013/072787, dated Apr. 24, 2014 (9 pages).
Irawan et al.. "Fabrication and performance testing of disposable micropump suitable for microfluidic chip," in Intl. Conf. on Biomedical and Pharmaceutical Engineering, Orchard Hotel, Singapore, Dec. 2006, pp. 252-255.
Jeong, et al. "Fabrication of a peristaltic PDMS micropump," Sensors and Actuators A, vol. 123-124, pp. 453-458, 2005.
Junwu et al., "Design and test of a high-performance piezoelectric micropurnp for drug delivery," Sensors and Actuators A, vol. 121, pp. 156-161, 2005.
Klonoff et al., "Insulin Pump Safety Meeting: Summary Report," Journal of Diabetes Science and Technoloity, 2009, pp. 396-402, vol. 3, No. 2.
Koch, et al., "PDMS and tubing-based peristaltic micropumps with direct actuation," Sensors and Actuators B, vol. 135. pp. 664-670, 2009.
Laser et al., "A review of micropurnps," J. Micromech. Microeng,, vol. 14(6), pp. R35-R64, 2004.
Lee et al., "Microfluidic mixing: A review," Int. J. Mol. Sci., 2011, pp. 3263-3287, vol. 12.
Li et al., "A high frequency high flow rate piezoelectrically driven MEMS micropump" in Proceedings IEEE Solid State Sensors and Actuators Workshop, Hilton Head, SC, Jun. 2000 (4 pages).
Ma et al., "Development and application of a diaphragm micropump with piezoelectric device," Microsyst. Technol., vol. 14, pp. 1001-1007, 2008.
Manz et al., "Miniaturized total chemical analysis systems: a novel concept for chemical sensing," Sensors and Actuators B, vol. 1, pp. 244-248, 1990.
Meece et al., "Effect of Insulin Pen Devices on the Management of Diabetes Mellitus," Am J Health-Syst. Pharm., 2008, pp. 1076-1082, vol. 65.
Melin et al., "A fast passive and planar liquid sample micromixer," Lab on a Chip. 2004, pp, 214-219, vol. 4.
Morrow, "Transdermal Patches Are More Than Skin Deep," Managed Care [Online]. Available at: http://www.managedcaremag.com/archives/0404/0404.biotech.html, Apr. 2004 (4 pages).
Mundell, "Antidepressant Cyrnbalta. Might Ease Chemo-Linked Pain." MSN Healthy Living, 2013 [Online]. Available at: http://health.msn.com/health-topics/cancer/antidepressant-cymbalta-might-ease-chemo-linked-pain (4 pages).
Nguyen et al,, "MEMS-micropumps: a review," Journal of Fluids Engineering, vol. 124, p. 384-392, 2002.
Nguyen et al., "Microfluidics for Internal Flow Control: Micropumps," in *Fundamentals and Applications of Microfluidics*, Norwood, MA: Artech House, Inc., 2002; pp. 293-341.

(56) References Cited

OTHER PUBLICATIONS

Nisar et al., "MEMS-based Micropumps in Drug Delivery and Biomedical Applications," Sensors and Actuators B, 2008, pp. 917-942, vol. 130.
Pallikaris, "Intracorneal mice-lens a minimally invasive option for presbyopia"; Aug. 10, 2010, p. 1, paragraph 003, accessed at http://www.rigneygraphics.com/clients/presbia/website/newsmedia/pdfs/press-osn-presbia.pdf (2 pages).
Pan et al, "A magnetically driven PDMS micropurnp with ball check-valves," J. Micromech. Microeng, vol. 15, pp. 1021-1026, 2005.
Rapp et al., "Liga, micropump for gases and liquids," Sensors and Actuators A, 1994, pp. 57-61, vol. 40, No. 1.
Richardson et al., "Peripheral Neuropathy: A True Risk Factor for Falls," The Journal of Gerontology: Series A, 1995, pp. 211-215, vol. 50, No. 4 (Abstract).
Roberts, "Blind Attack on Wireless Insulin Pumps Could Deliver Lethal Dose", Threatpost.com, The Kaspersky Lab Security News Service, Oct. 27, 2011 (2 pages).
Rosielle, "The Lidocaine Patch," Medical College of Wisconsin [Online]. Available: http://www.eperc.mcw.edu/EPERC/FastFactsIndex/ff_148.htm. [Accessed May 15, 2012] (3 pages).
Santra et al., "Fabrication and testing of a magnetically actuated micropurnp," Sensors and Actuators B, vol. 87, pp. 358-364, 2002.
Selam, "Evolution of Diabetes Insulin Delivery Devices," Journal of Diabetes Science and Technology, 2010, pp. 505-513, vol. 4, No. 3.
Shen et al., "Miniaturized PMMA ball-valve micropump with cylindrical electromagnetic actuator," Microelectronic Engineering, vol. 85, pp. 104-1107, 2008.
Singhal, et al., "Microscale pumping technologies for microchannel cooling systems," Appl. Mech. Rev., vol. 57(3), pp. 191-221, 2004.
Star Micronics Co. Ltd., "Precision products," Mar. 2009, [online]. Accessed at: http://www.star-m.jp/eng/products/precision/index/html, on Aug. 22, 2011 (4 pages).
Trenkle et al., "Normally-closed peristaltic rnicropump with reusable actuator and disposable fluidic chip," Sensors and Actuators B, vol. 154, pp. 137-141, 2011.
Tsai et al., "Review of MEMS-based drug delivery and dosing systems," Sensors and Actuators A, vol. 134, No. 2, pp. 555-564, 2007.
U.S. Appl. No. 13/174,598, filed Jun. 30, 2011, by Amirouche et al.: Non-Final Rejection, dated May 14, 2013.
U.S. Appl. No. 13/174,598, filed Jun. 30, 2011, by Amirouche et al.: Final Rejection, dated Oct. 3, 2013.
U.S. Appl. No. 13/174,598, filed Jun. 30, 2011, by Amirouche et al.: Notice of Allowance, dated Apr. 7, 2014.
U.S. Appl. No. 13/174,624, filed Jun. 30, 2011 by Amirouche et al.: Non-Final Rejection, dated Jun. 28, 2012.
U.S. Appl. No. 13/174,624, filed Jun. 30, 2011 by Amirouche et al.: Final Rejection, dated Nov. 21, 2012.
U.S. Appl. No. 13/174,624, filed Jun. 30, 2011 by Amirouche et al.: Non-Final Rejection, dated Feb. 8, 2013.
U.S. Appl. No. 13/174,624, filed Jun. 30, 2011 by Amirouche et al.: Final Rejection, dated Jul. 31, 2013.
U.S. Appl. No. 13/174,624, filed Jun. 30, 2011 by Amirouche et al.: Notice of Allowance, dated Feb. 5, 2014.
U.S. Appl. No. 13/174,643, filed Jun. 30, 2011 by Amirouche et al.: Non-Final Rejection, dated May 2, 2013.
U.S. Appl. No. 13/174,643, filed Jun. 30, 2011 by Amirouche et al.: Notice of Allowance, dated Oct. 21, 2013.
U.S. Appl. No. 13/308,899, filed Dec. 1, 2011, by Amirouche et al.: Non-Final Rejection, dated Aug. 8, 2013.
U.S. Appl. No. 13/308,899, filed Dec. 1, 2011, by Amirouche et al.: Notice of Allowance, dated Feb. 28, 2014.
U.S. Appl. No. 13/370,091, filed Feb. 9, 2012, by Amirouche et al.: Non-Final Rejection, dated Aug. 21, 2013.
U.S. Appl. No. 13/370,091, filed Feb. 9, 2012, by Amirouche et al.: Notice of Allowance, dated Mar. 25, 2014.
U.S. Appl. No. 13/649,202, filed Oct. 11, 2012, by Amirouche: Non-Final Rejection, dated Jun. 18. 2013.
U.S. Appl. No. 13/649,202, filed Oct. 11, 2012, by Amirouche: Final Rejection, dated Jan. 15, 2014.
Van Lintel et al., "A piezoelectric micropump based on micromachining of silicon," Sensors and Actuators A, vol. 15, p. 153-167, 1988.
Yadav et al., "Various Non-Injectable Delivery Systems for the Treatment of Diabetes Mellitus," Endocrine, Metabolic & Immune Disorders—Drug Targets, 2009, pp. 1-13. vol. 9, No. 1.
Yamahata et al. "A PMMA valveless micropump using electromagnetic actuation," Microfluid Nanofluid, vol. 1, pp. 197-207, 2005.
Zhu et al., "Optimization design of multi-material micropump using finite element methods" Sensors and Actuators A, vol. 149, pp. 130-135, 2009.

* cited by examiner

MULTI-PORTED DRUG DELIVERY DEVICE HAVING MULTI-RESERVOIR CARTRIDGE SYSTEM

BACKGROUND OF THE INVENTION

1. Field of the Invention

The present invention relates to the field of medical devices and, in particular, to devices for delivery of fluid medicament(s). More particularly, the present invention relates to a multi-ported drug delivery device having a cartridge system with multiple interconnected reservoirs that are independently actuated for delivery of medicament(s), and methods therefor.

2. Description of the Related Art

Diabetes is a disease caused by the body's failure to produce adequate insulin or the cell's failure to respond to insulin resulting in high levels of sugar in the blood. Type I diabetes is a form of diabetes mellitus that results from autoimmune destruction of insulin-producing beta cells of the pancreas. There is no cure for Type I diabetes and must be treated on a continuing basis. Type II diabetes is a metabolic disorder resulting from a combination of lifestyle, diet, obesity and genetic factors. The World Health Organization recently predicted that by 2030, 10% of the world's population of all ages would have either Type I or Type II diabetes. This translates to roughly 552 million people worldwide suffering from some form of this disease.

If left untreated, diabetes can cause numerous complications. Typically, treatment for diabetes required both repeated checking of blood glucose levels and several injections of insulin throughout the day. Major drawbacks of such treatment were the need to draw blood and test glucose levels throughout the day, improper or low dosage amounts of insulin, contamination of the insulin delivery system, or lifestyle restriction.

Diabetes may be controlled by insulin replacement therapy in which insulin is delivered to the diabetic person, usually by injection, to counteract elevated blood glucose levels. Recent therapies include the basal/bolus method of treatment in which basal, a long acting insulin medication, for example, Humalog® and Apidra®, is delivered via injection once every day. The basal provides the body with a relatively constant dose or a dosage profile prescribed by the physician of insulin throughout the day. At mealtime, an additional dose of insulin, or bolus, is administered based on the amount of carbohydrate and protein in the meal. Accurate calculations of various parameters including the amount of carbohydrates and proteins consumed, and the lapse in time since the last dosage are necessary to determine the appropriate dosage of insulin. The dosages are thus prone to human error and the method is ineffective when doses are skipped, forgotten or miscalculated. Exercise, stress and other factors may also affect the bolus calculations to be inaccurate.

To address these problems, insulin delivery devices or insulin pumps—both manual and programmable—were developed which seek to mimic the way a normal, healthy pancreas delivers insulin to the body. Insulin pumps can be programmed to deliver a continual basal dose of insulin and occasionally a bolus dose in response to a patient's meal intake and physical activities. Additionally, the number of times a patient is required to draw blood and test their glucose during the day is reduced, thus lessening the pain and inconvenience of this disease. Also, micro-doses of insulin that can be delivered by programmable insulin delivery devices are more easily tolerated and rapidly metabolized by the body and thus, more effective.

Exemplary delivery devices are described, for example, in U.S. Pat. Nos. 3,137,242; 3,498,228; 3,771,694; 4,340,048; 4,544,369; 4,552,561; 4,498,843; 4,657,486; and 5,858,001 and U.S. Publication No. 2010/0081993 A1. These delivery devices have numerous disadvantages including but not limited to—their overall size, propensity for leakage, high costs that made them unaffordable for long-term disease management or unavailable for most patients, potential risks of over or under dosage due to the pumping mechanism, and delivery of medication in quick bursts rather than diffused over time.

The second generation of delivery devices or pumps mainly featured activation by means of a piezoelectric actuator. Such pumps are described, for example, in U.S. Publication No. 2004/0176727. These pumps have several known disadvantages such as alignment issues related to the piezoelectric actuator, power and voltage requirements, overall design of the pump being limited by the shape of the piezoelectric actuator, and a single reservoir design.

Conventional insulin pumps are worn on the body and are connected to a patient via a cannula that is inserted somewhere on the patient's abdomen. The insulin is delivered under the skin and is absorbed into the body through the subcutaneous fat layer. Subcutaneous delivery of insulin takes advantage of the lack of blood flow in this area that allows for slower absorption of the medication through the dermal capillaries. Other methods of non-invasive insulin delivery are described in *Various Non-Injectable Delivery Systems for the Treatment of Diabetes Mellitus*, Yadav, N., et al., *Endocrine, Metabolic& Immune Disorders-Drug Targets*, 2009, Vol. 9(1):1-13. Because the pump is worn on the user's body at all times, and users desire to conceal it by clothing, these pumps should be small and unobtrusive. Further, the tubing connecting the pump to the user must be relatively short to reduce crystallization of the insulin medication.

Insulin pumps in the past have been quite large, some requiring the use of a shoulder bag to transport. Over time, they have become smaller in size and most pumps today are roughly the size of a deck of cards. Currently available insulin pumps include Animas OneTouch® Ping®, Deltec Cozmo®, Disetronic Accu-Chek Spirit®, Insulet OmniPod, Medtronic Paradigm™, Sooil USA Diabecare® II, and Nipro Amigo®. One recurring problem with most miniaturized ambulatory infusion pumps available today is that the amount of medication that can be stored in the reservoirs often cannot meet the needs of certain diabetic patients. Many Type II diabetics who require insulin often need more insulin per gram of carbohydrate due to a condition referred to as "insulin resistance." Additionally, many diabetic therapies include one or more medications delivered alternately or simultaneously. For this reason, a need exists for a delivery device that employs a plurality of reservoirs able to dispense medication at variable rates while maintaining a small overall size.

With the decreased size of the pump unit also comes a decreased size in the medication reservoir. This reduced reservoir size means more frequent refilling, greater potential for contamination of the reservoir, more frequent changes of the cannula and tubing, and greater expense overall in treating the condition. Frequent manual refilling of a medication reservoir can lead to an increased number of bubbles within the reservoir, which is a significant problem. Even very small bubbles, for example, of 10 microliters or less can displace enough fluid to equal a missed dose of 1 unit of medicament. Insulin medication itself can form bubbles when dissolved air is "outgassed" through normal changes in temperature or atmospheric pressure. Sooil USA Diabecare® II, Medtronic Paradigm™, Deltec Cozmo®, and Disetronic Accu-Chek Spirit® all require manual filling of the reservoir. The present invention overcomes the disadvantages of the existing systems by utilizing a volume that can exceed 300 u dual collapsible reservoirs prefilled with medicaments, with an option to redesign or re-conform the reservoirs to accommodate larger volumes.

Recent medical data suggests that a combination of insulin and another medication, such as glucagon, infused at different times or simultaneously, leads to better results in patients. Delivery of multiple medications is described, for example, in U.S. Publication Nos. 2007/0073230 A1; and 2011/0137287 A1. An advantage of the dual reservoirs of the present invention is that they can be manufactured to contain two dissimilar medicaments within the same disposable cartridge system, for instance, insulin in one reservoir and a different medicament in a second reservoir.

Finally, therapeutic infusion of medicaments is the prescribed treatment protocol for a variety of other diseases such as rheumatoid arthritis, autoimmune diseases, cancer, back and neck pain, joints, for the treatment of chronic pain, treatment of disc degenerative diseases, chemotherapy and tumor treatments. In the case of rheumatoid arthritis, the infusion therapy is usually administered over the course of several hours in a physician's office or infusion center and once or twice per month. This is a great inconvenience and expense for the patient that could be minimized by the use of an ambulatory infusion pump. The patient could be instructed on the procedure to self-administer the medication, insert a pre-filled medication reservoir at home and go about their normal daily routine. It has been shown that a lower dose of rheumatoid arthritis medication infused over a longer period of time produced better results with far fewer side effects.

Ambulatory infusion pumps that dispense a plurality of medications typically employ the use of multiple cannula, one cannula for each different medication and such pumps are described, for example, in U.S. Publication No. 2011/0137287 A1. The disadvantage of using a dual cannula is that there is a greater risk for infection and the problem with a y-shaped cannula is the awkwardness of the shape. Therefore, the need exists for an infusion pump that can deliver multiple medications from a plurality of reservoirs utilizing a multilumen infusion type cannula.

SUMMARY OF THE INVENTION

The present invention overcomes the disadvantages of the prior art and fulfills the needs noted above by providing a multi-ported drug delivery device having a pump driver system and a cartridge system.

More specifically, the present invention includes a multi-ported drug delivery device having a cartridge system featuring multiple, collapsible interconnected reservoirs that can be independently actuated for delivery of medicament(s).

More specifically, the present invention includes a multi-ported drug delivery device having a pump driver system, a cartridge system, a cannula and an insertion mechanism, and a plurality of conduits. The cartridge system of the multi-ported drug delivery device snaps into the pump driver system and is securely engaged to it.

The pump driver system includes a plurality of electromagnetic coils, for example, juxtaposed flat coils that drive a plurality of magnets on the cartridge system that apply alternate or continuous force to the pump membranes of the cartridge system. The pump driver system has a controller in communication with the electromagnetic coils to adjust the force applied by the electromagnetic coils, a power source, and a user interface configured to present information to a user. Additionally, the pump driver system may have a membrane switch that is communicatively linked to the controller, the membrane switch having a plurality of buttons for input of information. The multi-ported drug delivery device may include a touch screen, display and backlight assembly that is communicatively linked to the controller, the touch screen providing the user with an alternative and easy to use medium to input information to the multi-ported drug delivery device.

The plurality of conduits each includes a proximal end, a distal end, and a lumen extending from its proximal end to its distal end. The proximal ends of the plurality of conduits are securely engaged to the distal ends of the cannula and the insertion mechanism, and the distal ends are securely engaged to the proximal ends of a fluid outlet component of inlet/outlet members of the cartridge system. Alternatively, the plurality of conduits may have multilumen for delivery of multiple medications from a plurality of reservoirs of the cartridge system.

The present invention further includes a multi-ported drug delivery device having an integrated glucose monitor that enables the user to measure his or her blood glucose level by inserting a test strip into a strip connector housed on a circuit board of the pump driver system. An opening on the multi-ported drug delivery device enables the user to insert the test strip. The user is then able to apply a blood sample to the test strip and read his or her blood glucose level directly from a user interface display. Additionally, a controller on the circuit board can interpret the blood glucose readings and either make a dosage recommendation to the patient user or administer a dose based on user configuration and settings. Further, the blood glucose data, dosage amounts and other data can be stored in the controller to track, monitor and diagnose the patient user's history of insulin usage, their glucose measurements for a period of time, the cycle life of the pump driver system, energy usage, and any updates or downloads of software applications for using the multi-ported drug delivery device.

The present invention further includes a cartridge system having a plurality of reservoirs—for example, two to four— each with volume, preferably, of about 1.5 ml. Each of the plurality of reservoirs can be pre-filled with different medicaments and can be interconnected in any combination to serve as complement to one another. Further, any of the plurality of reservoirs can be a disposable, pre-filled and pre-pressurized reservoir that can be securely engaged to other elements of the cartridge system without removing, replacing or disengaging the cartridge system from the multi-ported drug delivery device. The basic mechanism of the multi-ported drug delivery device is to actuate each fluid chamber and membrane individually. The membrane of each individual actuation chamber is placed between two gold-plated neodymium-iron-boron disk magnets that are housed within each pump body insert. Each of the pump body inserts has a fluid receiving opening, a fluid discharge opening, a plurality of inlet channels, and a plurality of outlet channels. The pump body inserts are placed between two inlet/outlet members. Each of the inlet/outlet members has a fluid receiving opening, a fluid discharge opening, and a fluid outlet component. Additionally, each of the inlet/outlet members has a male part that securely engages to a female part of the reservoir forming an airtight seal. The reservoir, the fluid receiving opening of the inlet/outlet member and the pump body insert, the plurality of inlet channels, the plurality of outlet channels, and the fluid discharge opening of the pump body insert, the fluid discharge opening and the fluid outlet component of the inlet/outlet member are in fluid communication. The cartridge system further includes valve membranes that are placed between the fluid receiving openings of the pump body inserts and the inlet/outlet members, and between the fluid discharge openings of the pump body inserts and the inlet/outlet members. In addition, the cartridge system can have a plurality of valve cover channels and rosettes.

The valve membranes of the cartridge system can be active valves magnetically operated and integrated into the membrane housing to control the opening and closing of the output flow. A feedback control allows for automatic opening or closing of the valve membranes and dispersion of the medicament associated with the reservoir and the corresponding valve membrane.

The valve membranes can be dynamic valve membranes that are non-uniformly pre-stressed and having a base, a suspension part and a compliant deflection part. The valve membranes of the cartridge system can be formed, for example, of Silastic Q7-4840. The reservoirs can be formed, for example, of Silastic Q7-4840, or Medical Grade Polyisoprene. The pump body inserts and the inlet/outlet members can be formed, for example, of clear polypropylene homopolymer, or clear Medical Grade Acrylic such as OPTIX CP-927. The pump membrane can be formed, for example, of Silastic Q7-4840.

The present invention also includes a cartridge system having a plurality of orifices to fill or re-fill a plurality of medicaments in the reservoirs. The plurality of orifices can be located on the reservoirs, or on the inlet/outlet members, the plurality of orifices being in fluid communication with the reservoirs.

The present invention further includes a method of delivering medicament using a multi-ported drug delivery device having a cartridge system with multiple reservoirs. The method includes the steps of providing a multi-ported drug delivery device having a pump driver system and a multi-reservoir cartridge system, loading a plurality of pre-filled reservoirs containing fluid medicament into the cartridge system, engaging securely with the cartridge system and the pump driver system, selecting various parameters on a user interface of the pump driver system including selecting pre-determined values or specifying user-defined values for various parameters, and connecting an infusion set to the multi-ported drug delivery device.

The method of delivering medicament using the multi-ported drug delivery device includes the additional steps of placing an inset of the infusion set on a body part of a patient, attaching the infusion set to the patient's body, and switching on the multi-ported drug delivery device.

The method of delivering medicament using the multi-ported drug delivery device wherein the step of connecting an infusion set to the multi-ported drug delivery device further includes the steps of connecting one end of a Y-catheter to an outlet component of an inlet/outlet member, and delivering fluid medicament at a given rate. The step of delivering fluid medicament at a given rate can further include delivering fluid medicament at a controlled and continuous rate for a pre-determined or user-defined period of time. Alternatively, the step of delivering fluid medicament at a given rate can further include delivering fluid medicament at a programmable rate that is regulated by the patient.

The present invention also includes a method of delivering medicament using the multi-ported drug delivery device having the cartridge system. The method includes the steps of providing a multi-ported drug delivery device having a pump driver system and a multi-reservoir cartridge system, loading a plurality of reservoirs to the cartridge system, using an instrument to inject a plurality of fluid medicaments into the plurality of reservoirs, engaging securely the cartridge system and the pump driver system, selecting various parameters on a user interface of the pump driver system including selecting pre-determined values or specifying user-defined values for various parameters, and connecting an infusion set to the multi-ported drug delivery device. The step of connecting an infusion set to the multi-ported drug delivery device further includes the steps of connecting one end of a Y-catheter to an outlet component of an inlet/outlet member, and delivering fluid medicament at a given rate. The step of delivering fluid medicament at a given rate can further include delivering fluid medicament at a controlled and continuous rate for a pre-determined or user-defined period of time. Alternatively, the step of delivering fluid medicament at a given rate can further include delivering fluid medicament at a programmable rate that is regulated by the patient.

The present invention further includes a multi-ported drug delivery device having a pump driver system, a multi-reservoir cartridge system, a cannula and an insertion mechanism, and a plurality of conduits. The pump driver system includes a driver that drives the magnets that applies forces to the pump membranes of the cartridge system, a controller in communication with the pump to adjust the force applied by the driver, a power source, and a user interface configured to present information to a user. The cartridge system of the device snaps into the pump driver system and is securely engaged to it. The plurality of conduits each includes a proximal end, a distal end, and a lumen extending from its proximal end to its distal end. The proximal ends of the plurality of conduits are securely engaged to the distal ends of the cannula and the insertion mechanism, and the distal ends are securely engaged to the proximal ends of the fluid outlet component of the inlet/outlet members of the cartridge system.

Other features and advantages of the present invention will become apparent from the following description of the invention, which refers to the accompanying drawings.

DETAILED DESCRIPTION OF THE PREFERRED EMBODIMENTS

Disclosed embodiments relate to a multi-ported drug delivery device for delivery of medicament, the device having a pump driver system, and a multi-reservoir cartridge system.

The term "fluid" is defined as a state of matter or substance (liquid or gas) whose particles can move about freely, and has no fixed shape or conform to the shape of their containers.

The term "channel" is defined as a passage for fluids to flow through.

The term "medicament" is defined as a substance used in therapy, a substance that treats, prevents or alleviates the symptoms of disease, a medicine in a specified formulation, or an agent that promotes recovery from injury or ailment.

The term "user" or "patient user" is defined as a person who uses or operates the drug delivery device.

Figure 10A:
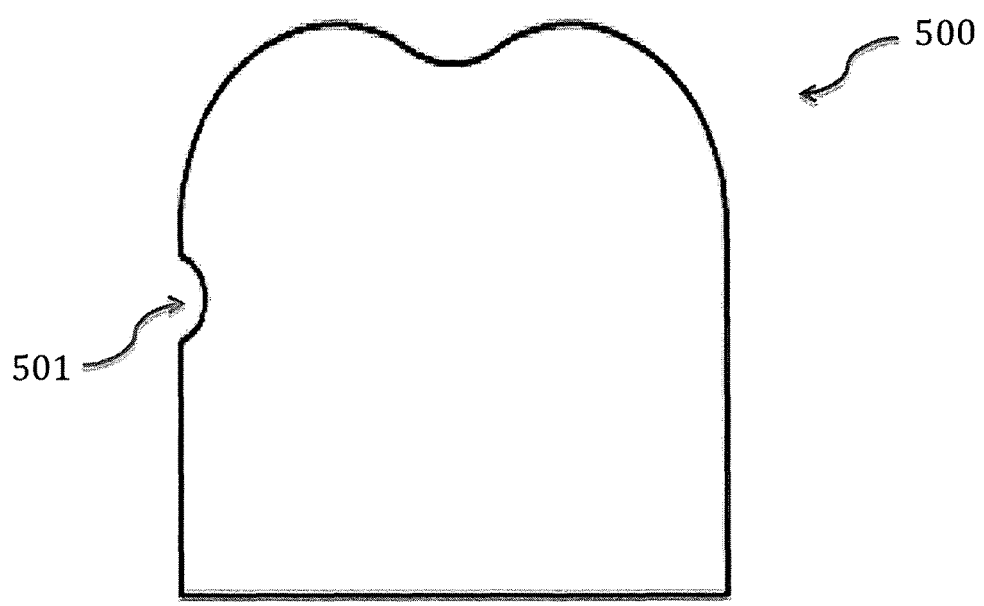
FIGS. 10A-10B illustrate the rear and perspective views of a pump membrane of the cartridge system in accordance with an embodiment of the present invention.
Figure 10B:
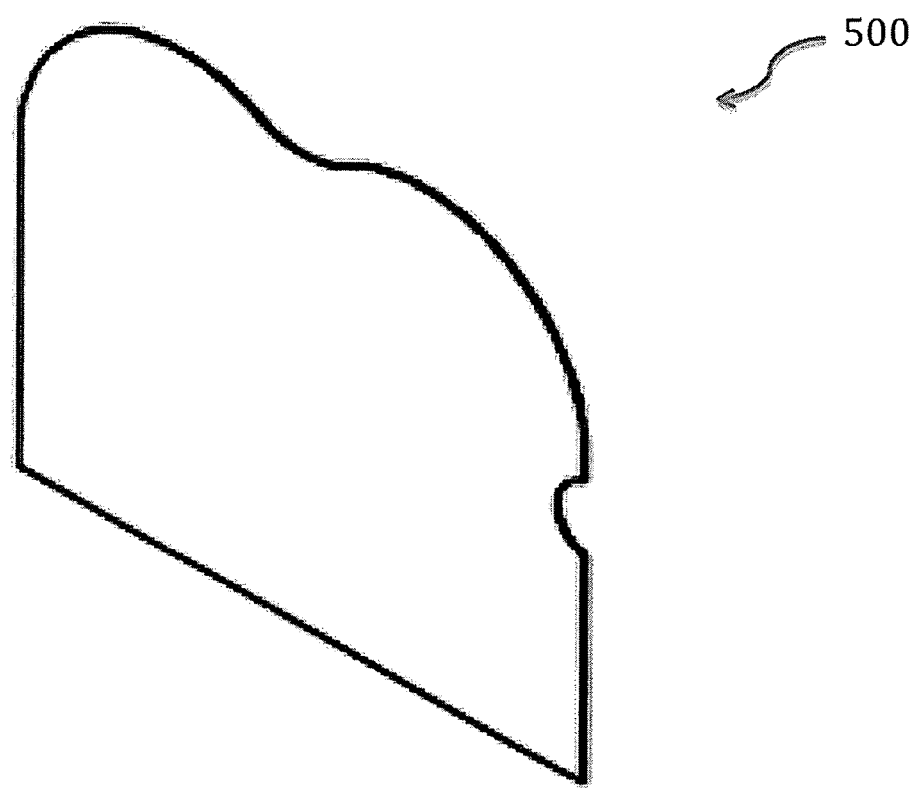

Referring now to the drawings, where like elements are designated by like reference numerals, FIGS. 1A-1F illustrate a cartridge system 100 in accordance with an embodiment of the invention. The cartridge system 100 includes a plurality of pump body inserts 200a, 200b, a plurality of inlet/outlet members 400a, 400b, a plurality of clamshells 600a, 600b, a plurality of reservoirs, 800a, 800b, 800c, 800d, a plurality of valve membranes 700 (FIG. 12) and a plurality of pump membranes 500 (FIG. 10A-B). The overall dimensions of the cartridge system 100 are preferably 2.061" (length)×0.525" (width)×1.725" (height).

TABLE 1

Cartridge System of the Present Invention

Figure 11:
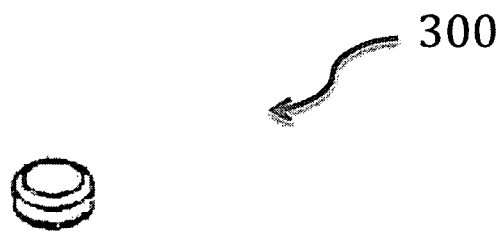
FIG. 11 illustrates the perspective view of a magnet of the cartridge system in accordance with an embodiment of the present invention.
Figure 12:
FIG. 12 illustrates the perspective view of a valve membrane of the cartridge system in accordance with an embodiment of the present invention.

| Pump Body Insert | |
|---|---|
| Overall dimensions: | 0.99" (length) × 1.23" (width) × 0.09" (height) |
| Basic shape: | Shape as shown in FIGS. 2A-3E, and having a plurality of fluid channels, a plurality of fluid receiving openings, and a plurality of fluid discharge openings |
| Material: | Clear acrylic |
| Number: | Preferably, two |
| Inlet/Outlet Member | |
| Overall dimensions: | 0.51" (length) × 1.99" (width) × 0.20" (height) |
| Basic shape: | Shape as shown in FIGS. 4A-5G, and having a plurality of fluid receiving openings, a plurality of discharge openings, and a plurality of fluid outlet components |
| Material: | Clear acrylic |
| Number: | Preferably, two |
| Clamshell | |
| Overall dimensions: | 0.79" (length) × 1.56" (width) × 0.22" (height) |
| Basic shape: | Shape as shown in FIGS. 6A-7F, and having a plurality of electromagnetic coil openings, a locking pin opening, and an insertion sensor opening |
| Material: | PVC |
| Number: | Preferably, two |
| Reservoir | |
| Overall dimensions: | 0.56" (length) × 0.76" (width) × 0.26" (height) |
| Basic shape: | Shape as shown in FIGS. 8A-8G, and made of a material from a group consisting of elastomer, and the material having property such that geometry is deformable |
| Material: | Silastic Q7-4840 or Medical Grade Polyisoprene |
| Number: | Preferably, four |
| Magnets | |
| Overall dimensions: | 0.13" (diameter) × 0.06" (height) |
| Basic shape: | Cylindrical, as shown in FIG. 11 |
| Material: | Neodymium-iron-boron grade N42 magnets, gold plated (NdFeB) |
| Number: | Preferably, four |
| Pump Membrane | |
| Overall dimensions: | 0.99" (length) × 1.23" (width) × 0.005" (height) |
| Basic shape: | Shape as shown in FIGS. 10A-B |
| Material: | Silastic Q7-4840 |
| Number: | Preferably, one |
| Valve Membrane | |
| Overall dimensions: | 0.19" (diameter) × 0.04" (height) |
| Basic shape: | Cylindrical, as shown in FIG. 12 |
| Material: | Silastic Q7-4840 or Medical Grade Polyisoprene |
| Number: | Preferably, eight |

Referring to FIGS. 2A-2D, a first pump body insert 200a having a plurality of fluid receiving openings 202a, 202b, and fluid discharge openings 201a, 201b is shown. The first pump body insert 200a also includes a plurality of fluid channels 206a, 207a, 207b, 208a, 209a, 209b, for example, two output channels 206a, 208a, and four input channels 207a, 207b, 209a, 209b. The plurality of input channels 207a, 207b, 209a, 209b and output channels 206a, 208a are in fluid communication with the fluid receiving openings 202a, 202b and fluid discharge openings 201a, 201b, respectively. The plurality of input channels 207a, 207b, 209a, 209*b* and output channels 206*a*, 208*a* are designed to provide membrane support thereby preventing deformation and reverse the flow of fluids. The first pump body insert 200*a* has a plurality of openings 205*a*, 205*b* to house magnets 300 (FIG. 11). Apertures 214*a*, 214*b*, 214*c*, 214*d* can be used to align and/or secure the first pump body insert 200*a* to other elements of the cartridge system 100.

The advantages of using polymer materials to make the pump body inserts 200*a*, 200*b*, inlet/outlet members 400*a*, 400*b*, clamshells 600*a*, 600*b*, and reservoirs 800*a*, 800*b*, 800*c*, 800*d* is that they can be made in almost any size, designed in almost any way, and manufactured with biocompatible materials. The methods used in the manufacture of the polymer components as well as the arrangement and design of the cartridge system lends itself being readily adaptable to commonly used sterilization techniques such as gamma irradiation, steam sterilization, or fluid chemical sterilization.

The second pump body insert 200*b*, shown in FIGS. 3A-3E, is substantially symmetrical in geometry to the first pump body insert 200*a* except having a differing number in the plurality of output and input channels, for example, four output channels 206*b*, 206*c*, 208*b*, 208*c*, and two input channels 207*c*, 209*c*. The first and second pump insert bodies 200*a*, 200*b*, are preferably made of clear acrylic.

The cartridge system 100 has a pump membrane 500 (FIGS. 10A-B). The pump membrane 500 (FIGS. 10A-B) is a biocompatible elastomer membrane, preferably made of Silastic Q7-4840. The pump membrane 500 (FIGS. 10A-B) is placed between four disk magnets 300 (FIG. 11), which are housed within a plurality of openings 205*a*, 205*b* of the first and second pump body inserts 200*a*, 200*b*. The disk magnets 300 are preferably gold-plated neodymium-iron-boron grade N42 magnets. The volume of flow of fluid medicaments in the cartridge system 100 is related to the diameter of the magnets 300 and the stroke length. The stroke length can be electromagnetically controlled and monitored by a driver feedback system.

Referring to FIGS. 4A-4G, a first inlet/outlet member 400*a* having a plurality of fluid receiving openings 404*a*, 404*b* and fluid discharge openings 403*a*, 403*b* is shown. The inlet/outlet member 400*a* has a fluid outlet component 401 having a proximal end (not shown), a distal end (not shown) and a cylindrical body connecting the distal and the proximal ends to form a hollow for receiving fluid medicament. In one embodiment, the proximal end can preferably have a tapered end with a luer slip. A plurality of outlet channels 401*a*, 401*b* are in fluid communication with the fluid discharge openings 403*a*, 403*b*. The inlet/outlet member 400*a* includes male parts 402*a*, 402*b* that securely engage to the female part 802 (FIG. 8A) of the reservoirs 800*a*, 800*b* respectively. Apertures 407*a*, 407*b*, 407*c*, 407*d* can be used to align and/or secure the first inlet/outlet member 400*a* to other elements of the cartridge system 100. The male parts 402*a*, 402*b* of the inlet/outlet members 400*a*, 400*b* can have tooth-like channels to ensure that a low resistance path for fluid flow exists for all configurations of the reservoirs 800*a*, 800*b*, 800*c*, 800*d*.

The second inlet/outlet member 400*b*, shown in FIGS. 5A-5G, is substantially symmetrical in geometry to the first inlet/outlet member 400*a*. Inlet/outlet members 400*a*, 400*b* are preferably made of clear acrylic. The male parts of the inlet/outlet members can have tooth-like channels to ensure that a low resistance path for fluid flow exists for all configurations of the reservoirs.

Referring to FIGS. 6A-6G, a first clamshell 600*a* having a plurality of openings 602*a*, 602*b* to house electromagnetic coils, for example, juxtaposed flat coils are shown. The first clamshell 600*a* has a locking pin opening to secure the first and second pump body inserts 200*a*, 200*b* in a preferable position while the cartridge system 100 is in operation. The first clamshell 600*a* has a sensor opening 606 at a location substantially opposite the locking pin opening 601. The sensor opening 606 houses a detection sensor to help control the activation of the electromagnetic coils. Apertures 605*a*, 605*b*, 605*c* can be used to align and/or secure the first clamshell 600*a* to other elements of the cartridge system 100. The first clamshell 600*a* has flanges 607*a*, 607*b* to facilitate a smooth and preferable insertion of the cartridge system 100 into the first clamshell 600*a*.

Figure 1A:
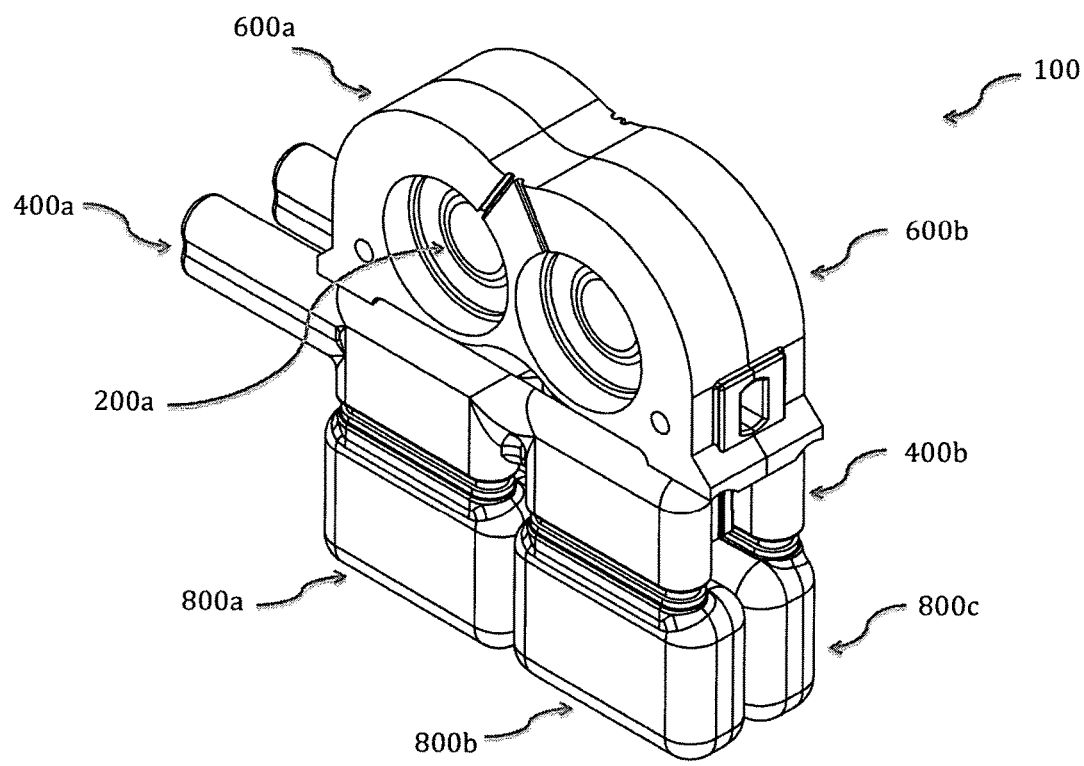
FIGS. 1A-1F illustrate the perspective, rear, bottom, left, right, and top views, respectively, of a cartridge system in accordance with an embodiment of the present invention.
Figure 1B:
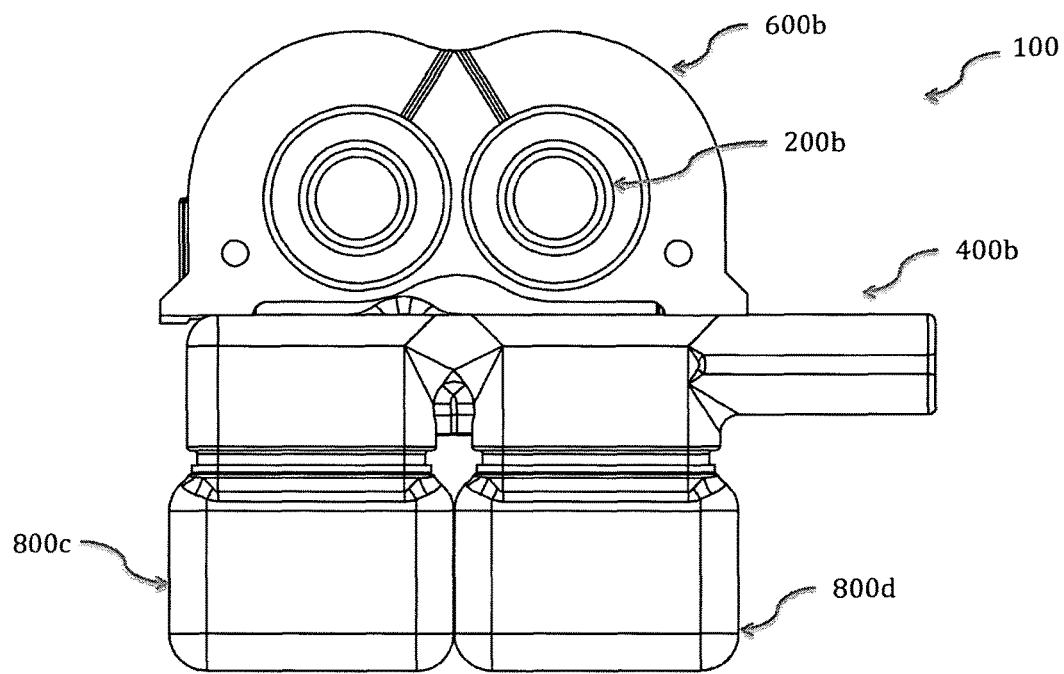
Figure 1C:
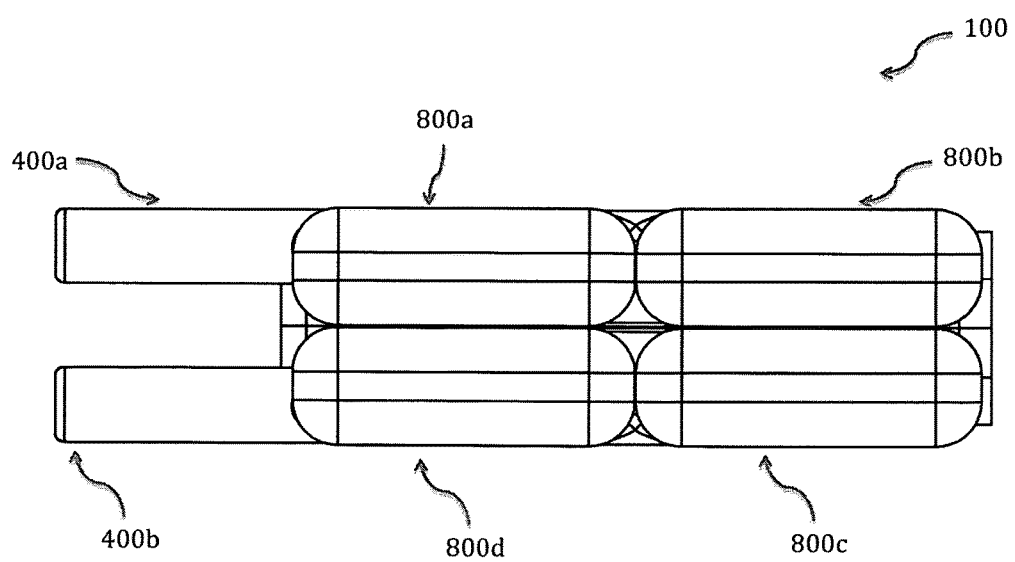
Figure 1D:
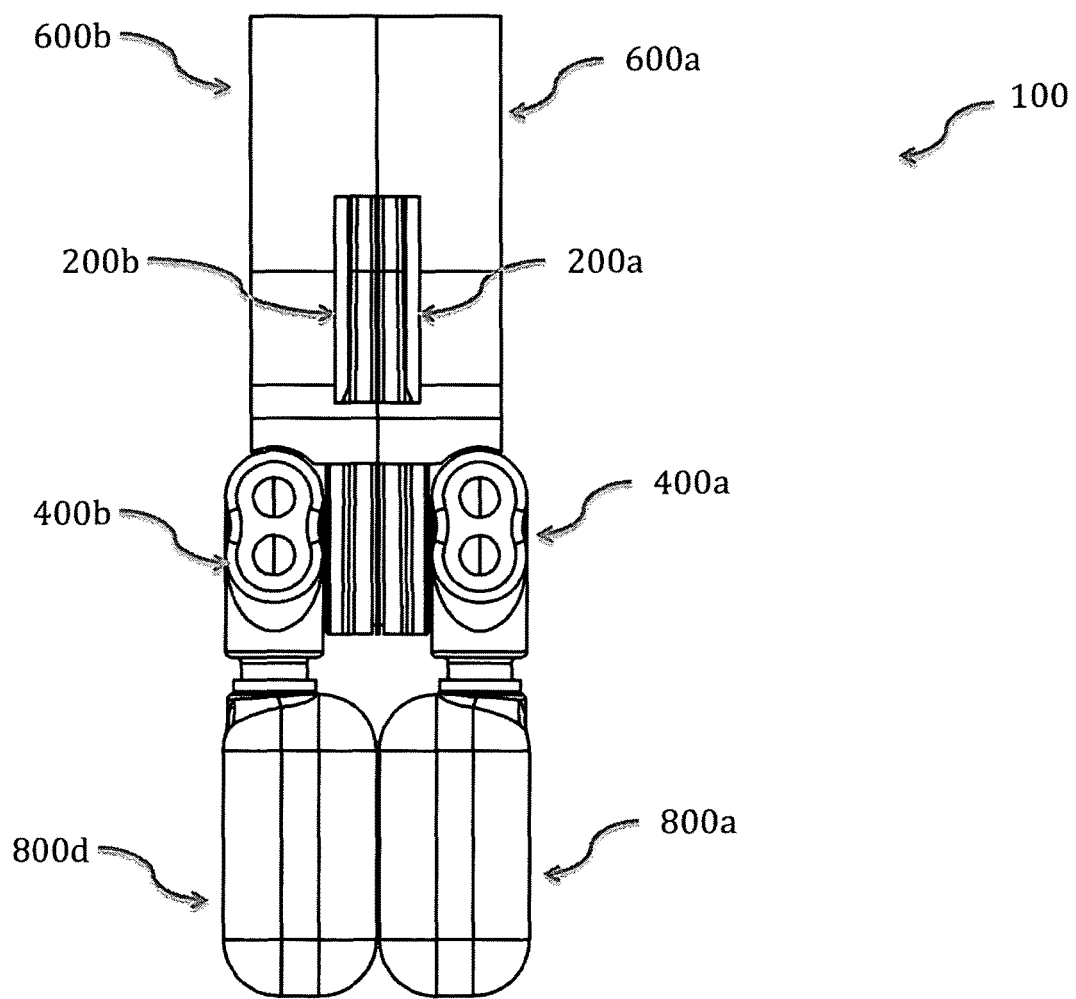
Figure 1E:
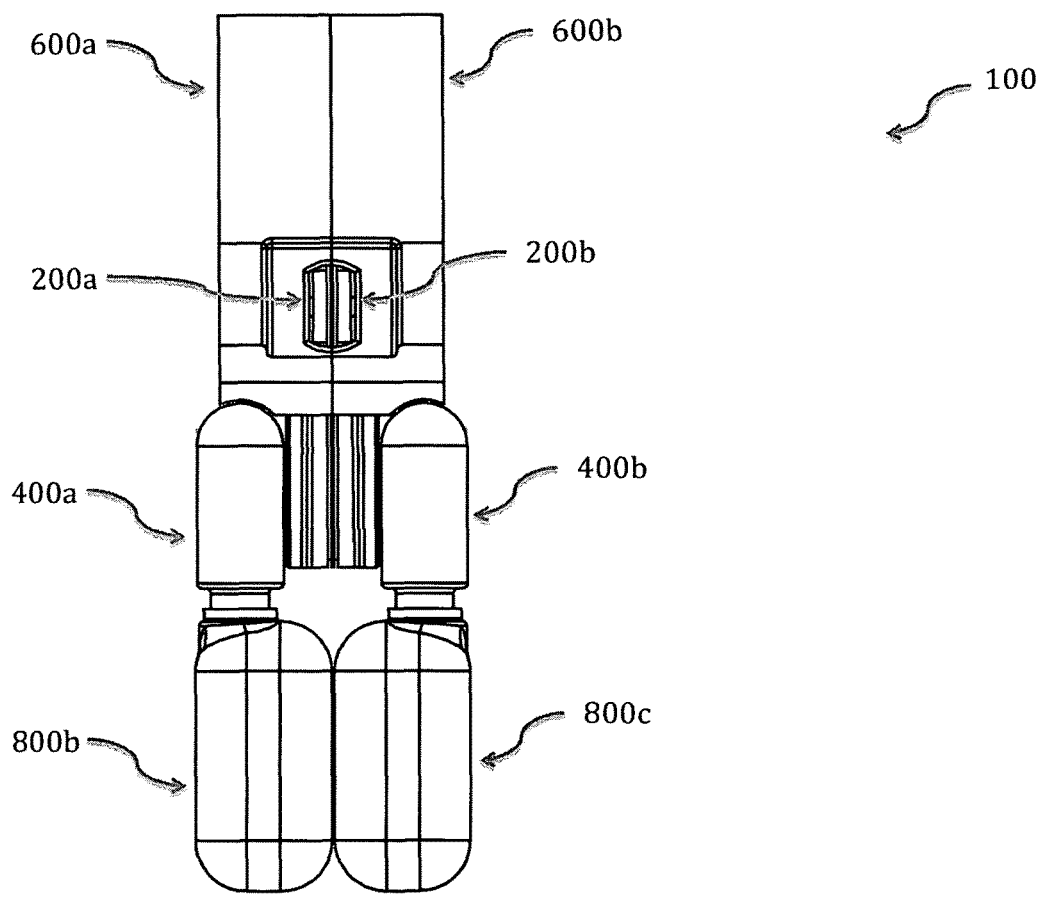
Figure 1F:
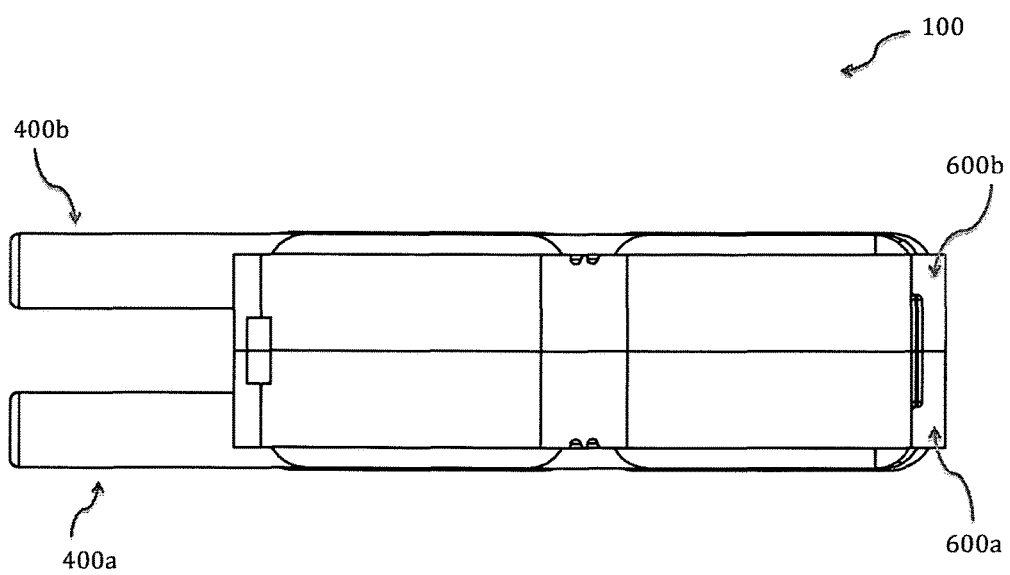
Figure 2A:
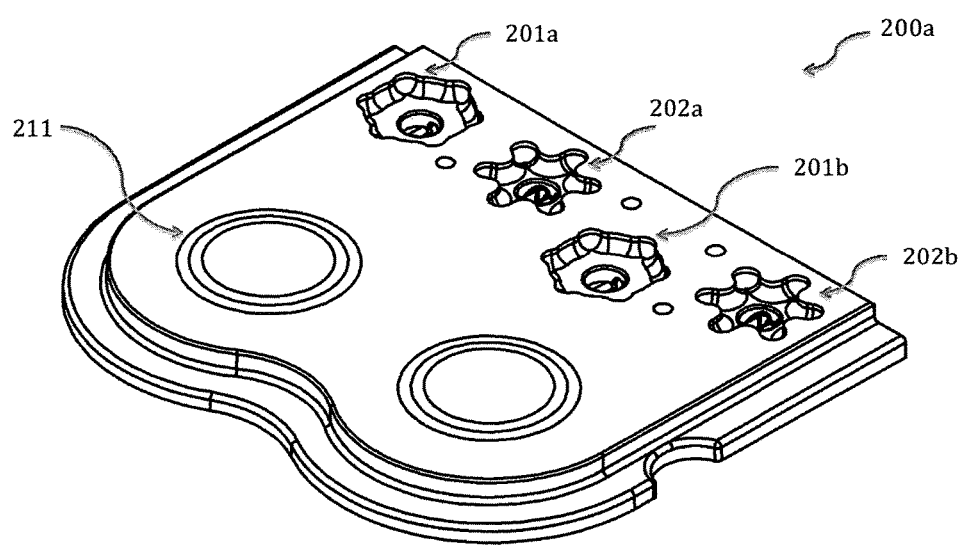
FIGS. 2A-2D illustrate the perspective, top, bottom, rear, and front views, respectively, of a first pump body insert of the cartridge system in accordance with an embodiment of the present invention.
Figure 2B:
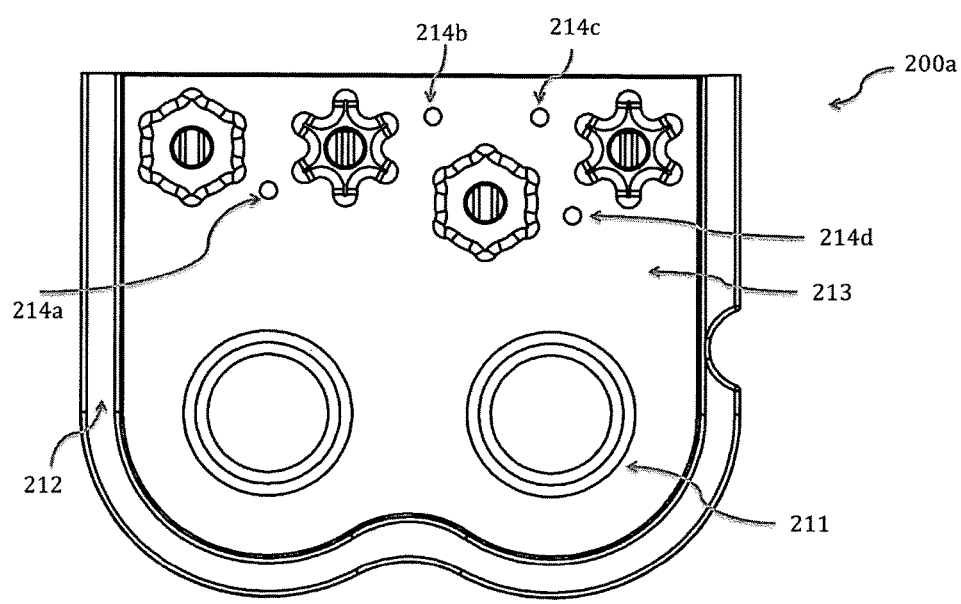
Figure 2C:
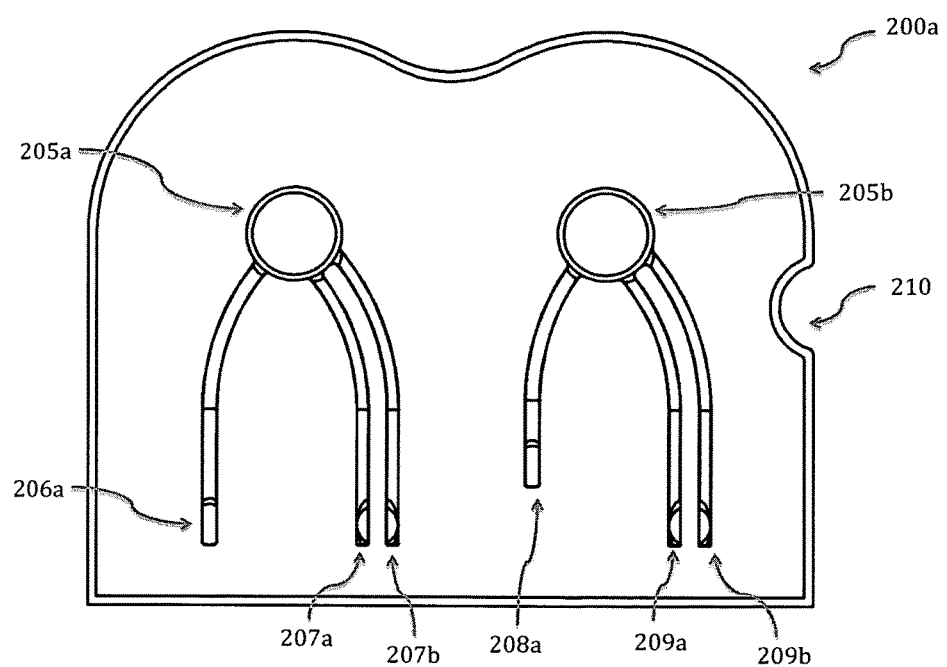
Figure 2D:
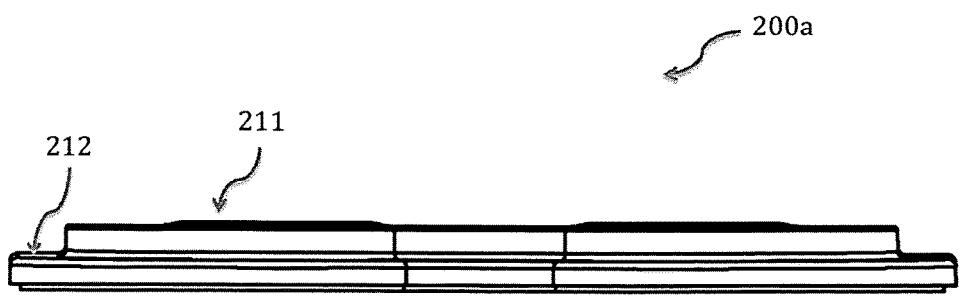
Figure 3A:
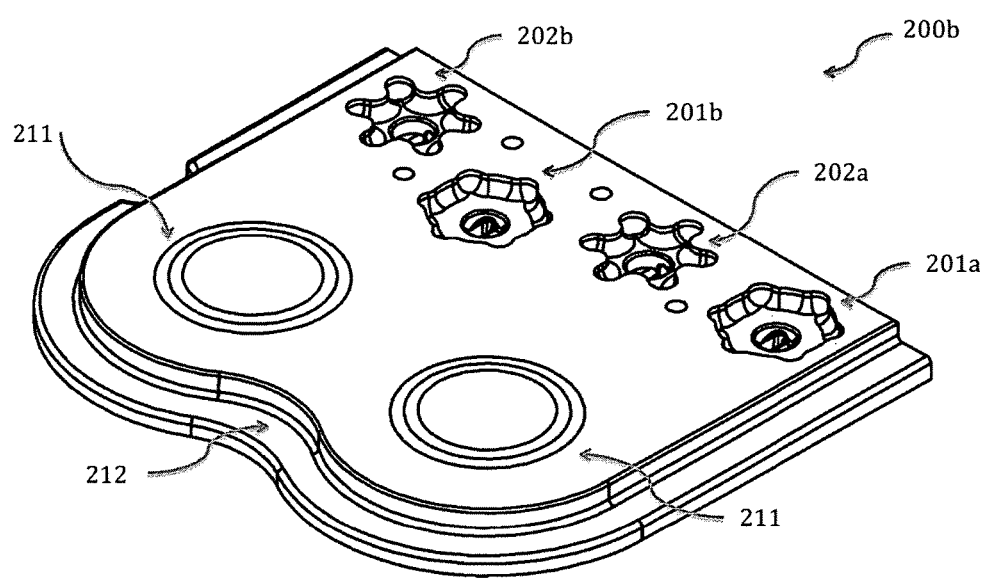
FIGS. 3A-3F illustrate the perspective, top, bottom, front, rear, and right side views, respectively, of a second pump body insert of the cartridge system in accordance with an embodiment of the present invention.
Figure 3B:
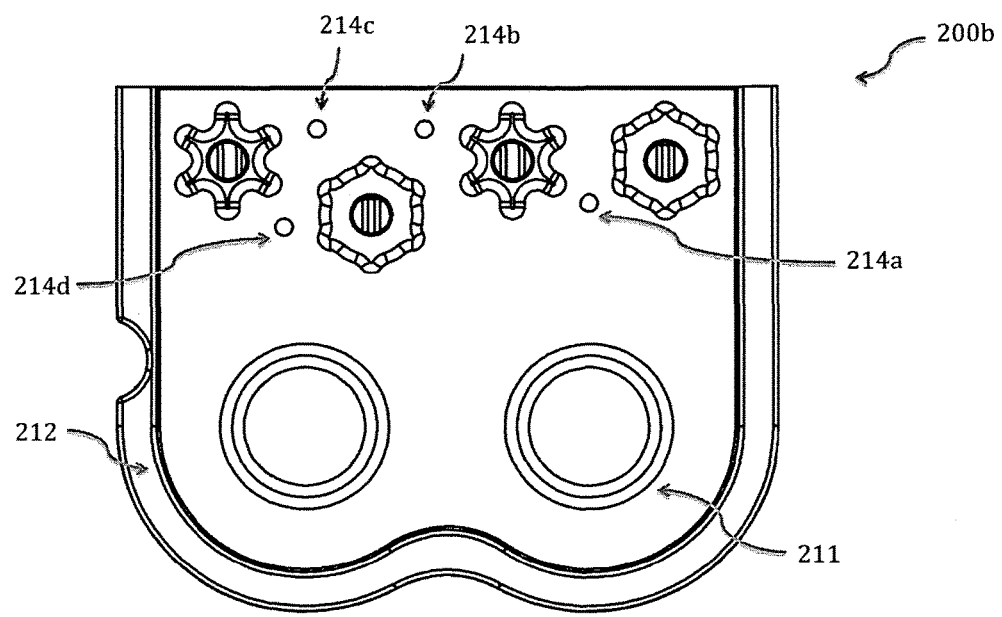
Figure 3C:
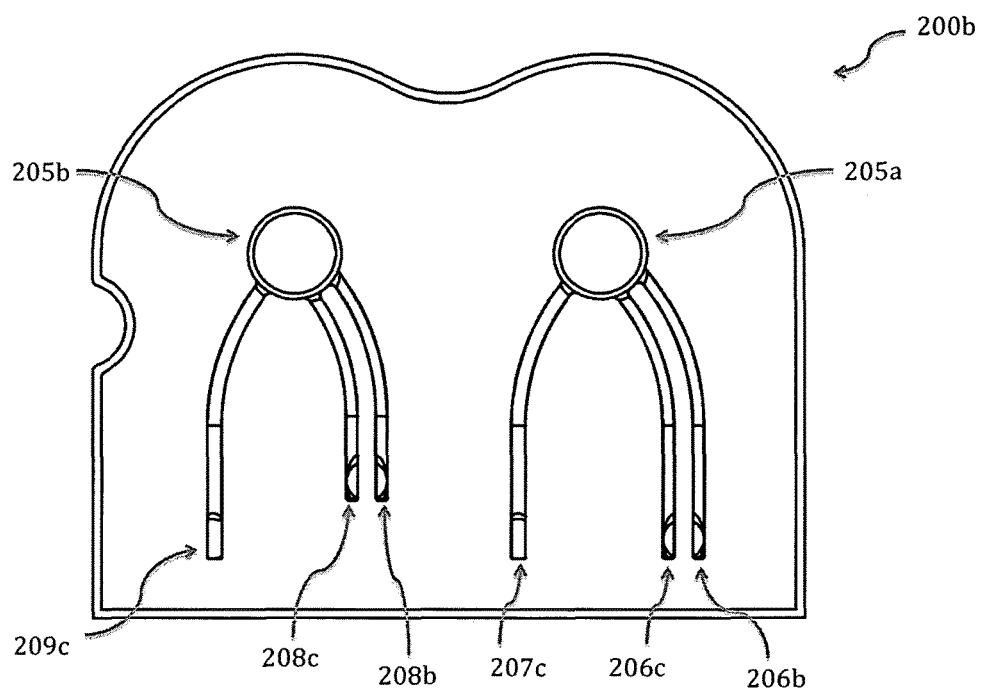
Figure 3D:
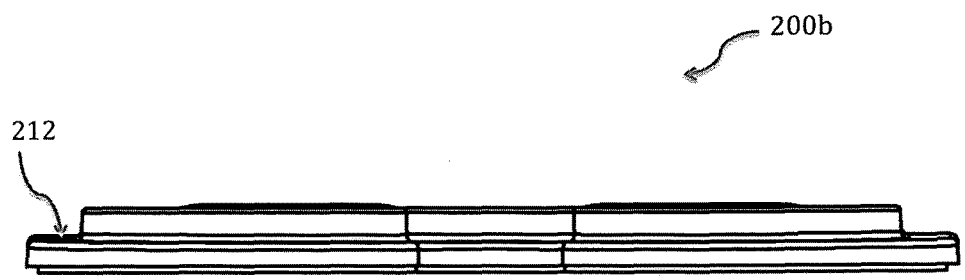
Figure 3E:
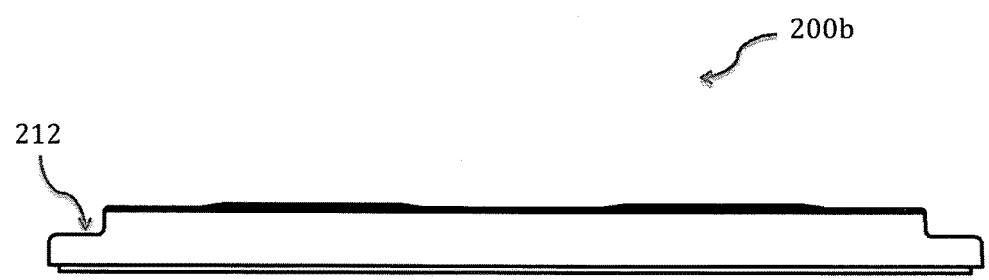
Figure 3F:
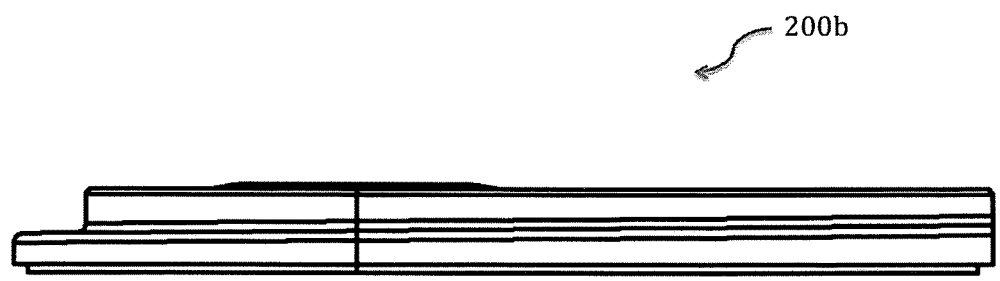
Figure 4A:
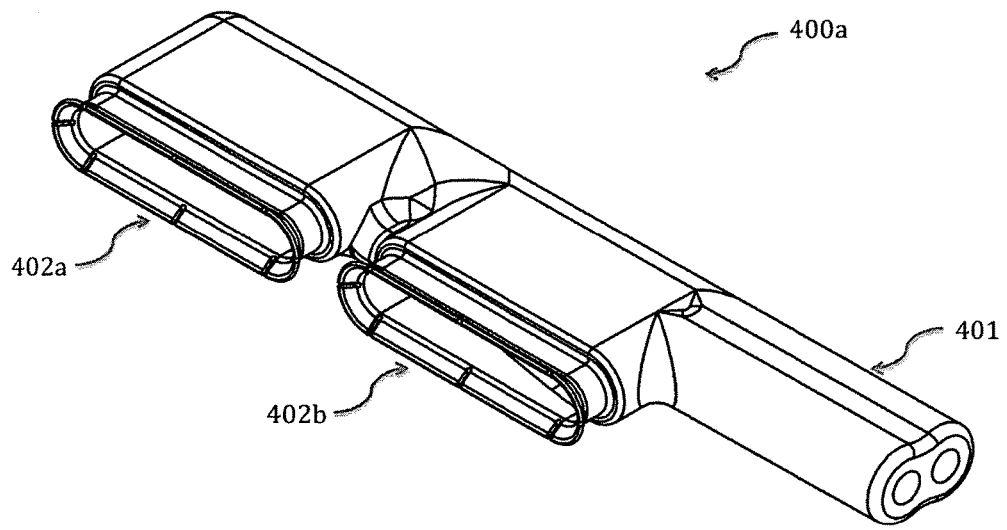
FIGS. 4A-4G illustrate the perspective, top, front, right side, left side, rear, and bottom views, respectively, of a first inlet/outlet pair member of the cartridge system in accordance with an embodiment of the present invention.
Figure 4B:
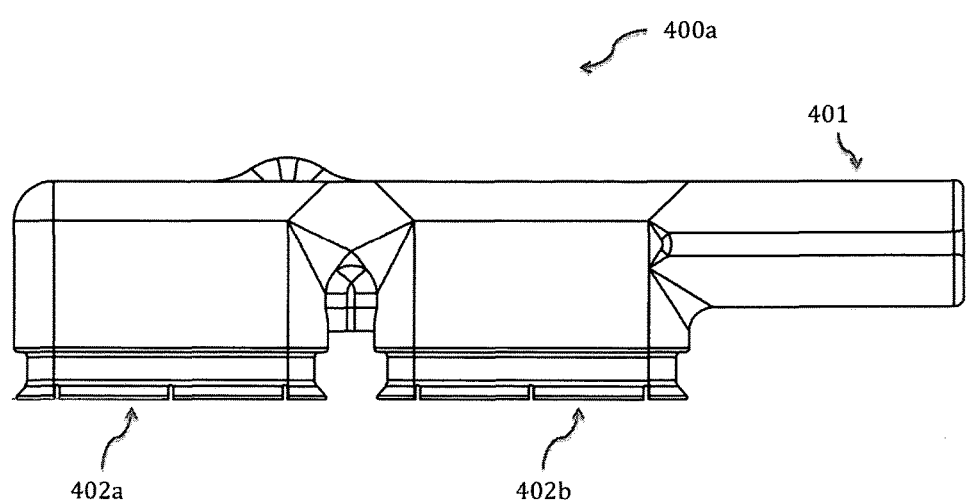
Figure 4C:
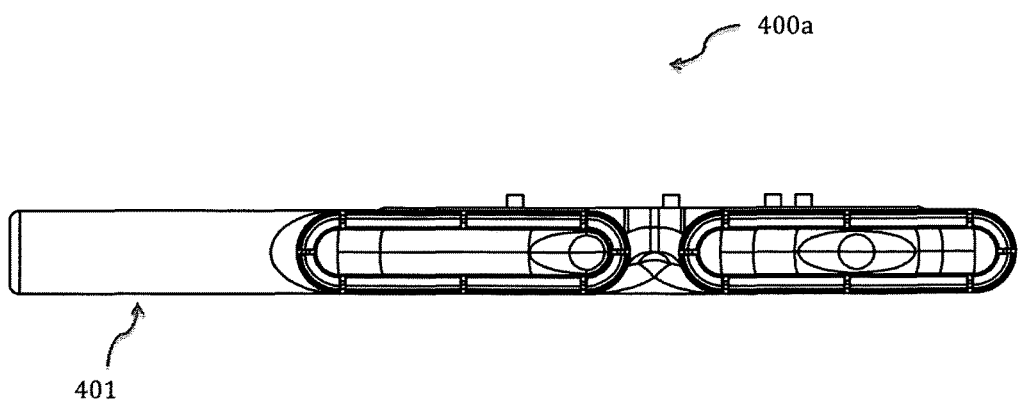
Figure 4D:
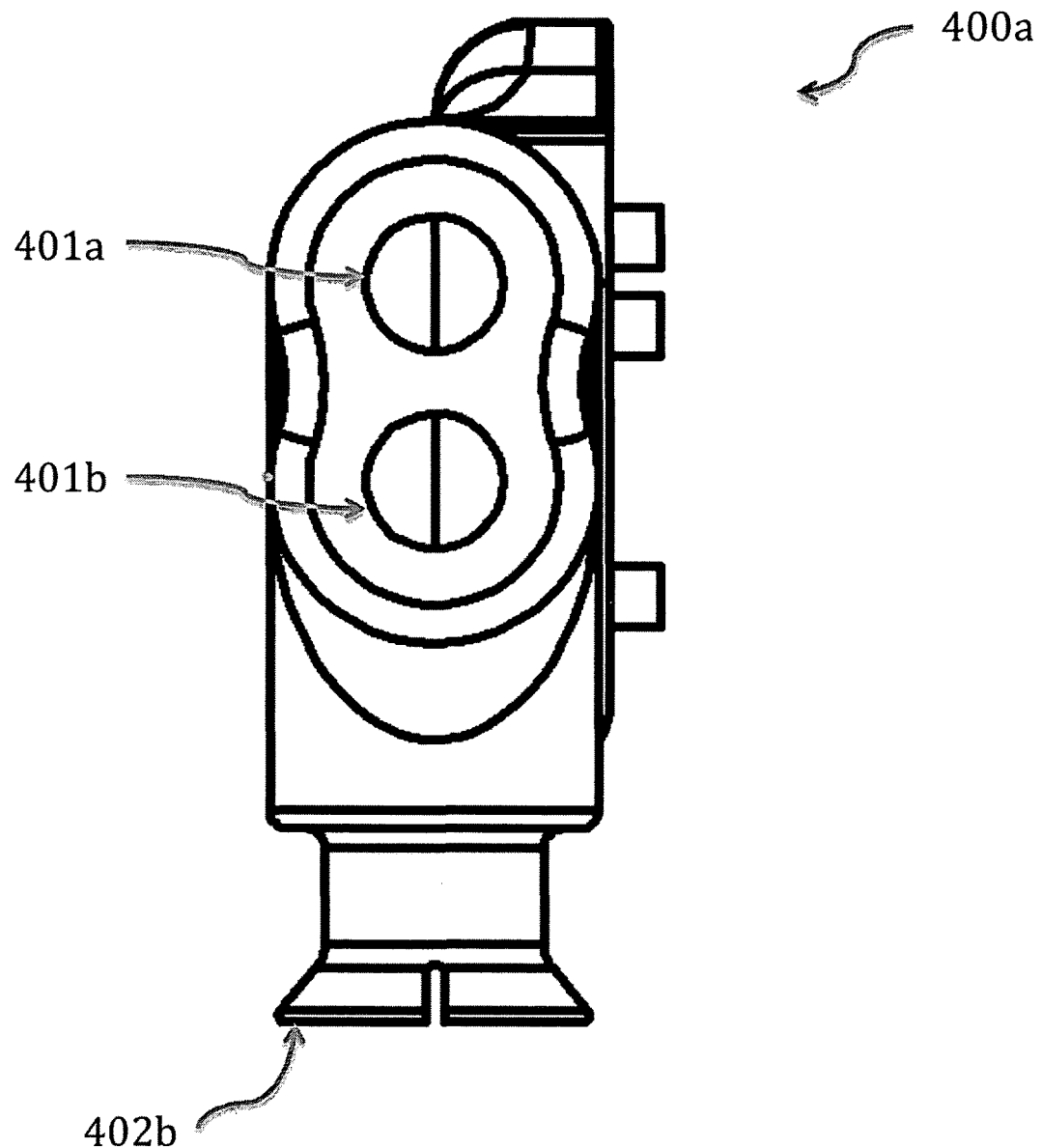
Figure 4E:
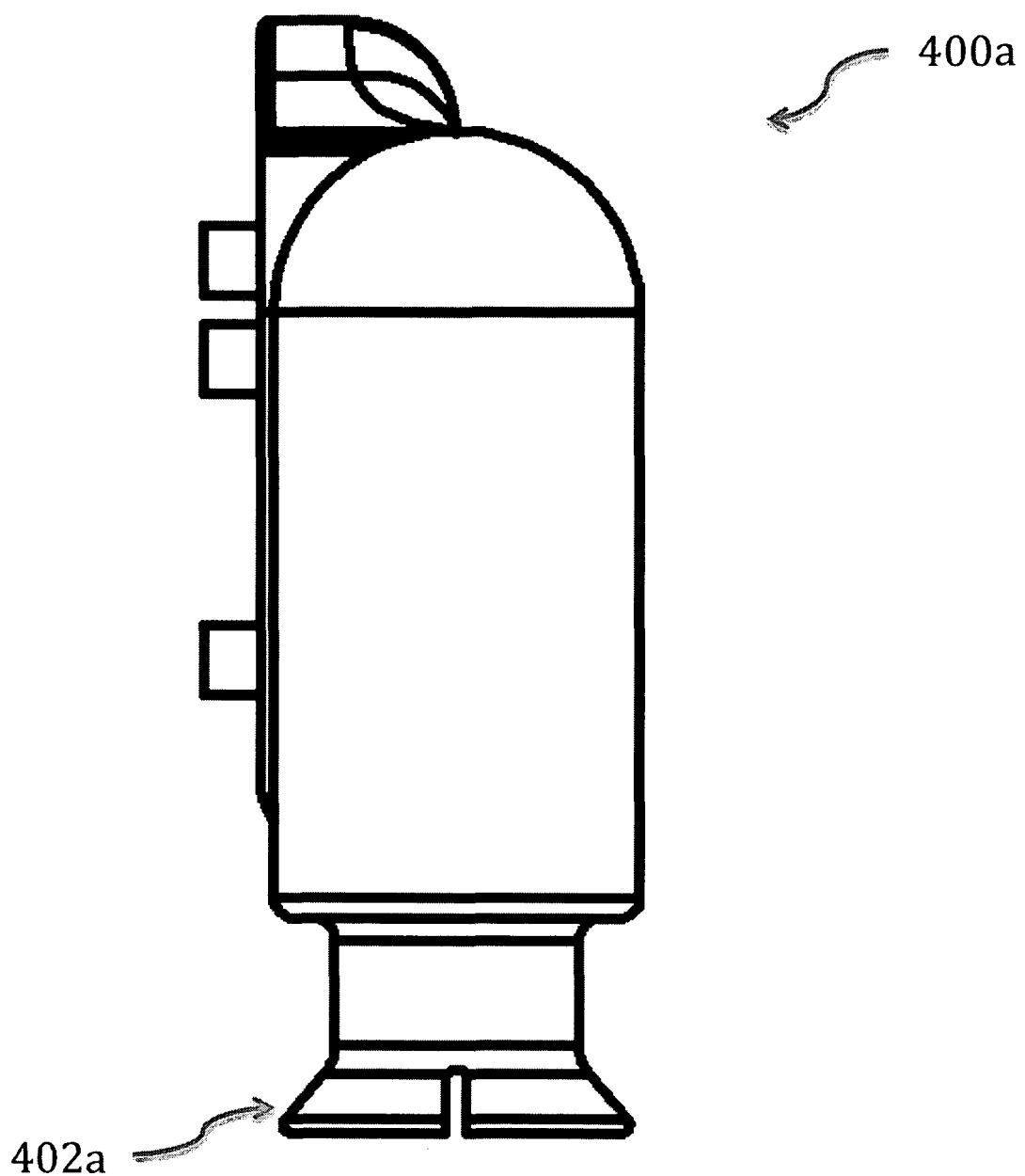
Figure 4F:
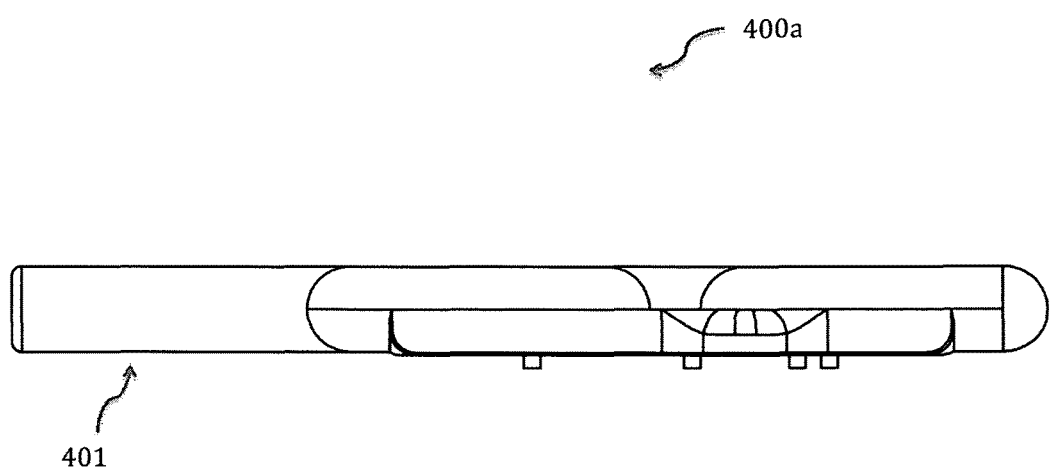
Figure 4G:
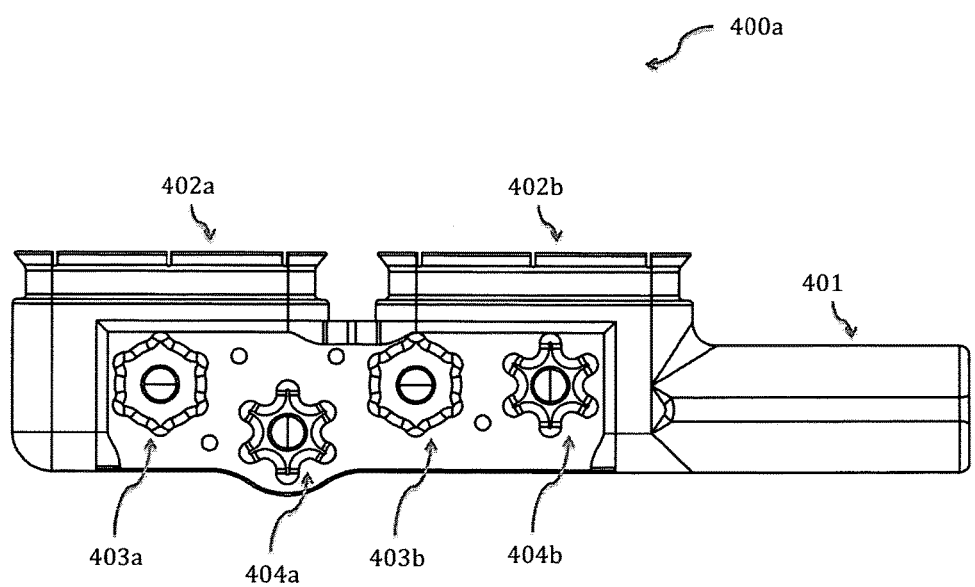
Figure 5A:
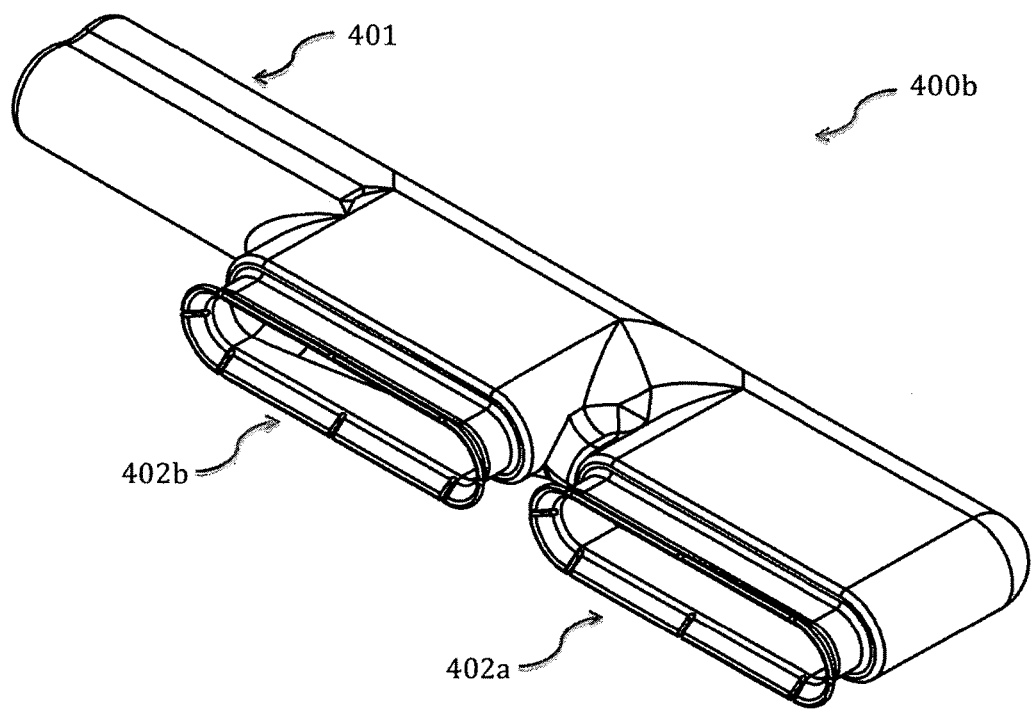
FIGS. 5A-5G illustrate the perspective, bottom, front, right side, left side, rear, and top views, respectively, of a second inlet/outlet pair member of the cartridge system in accordance with an embodiment of the present invention.
Figure 5B:
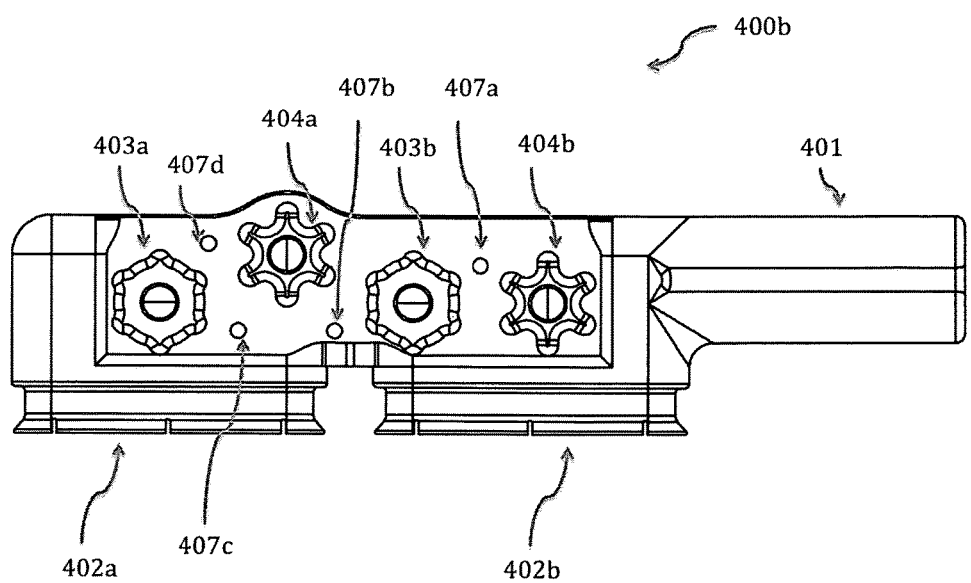
Figure 5C:
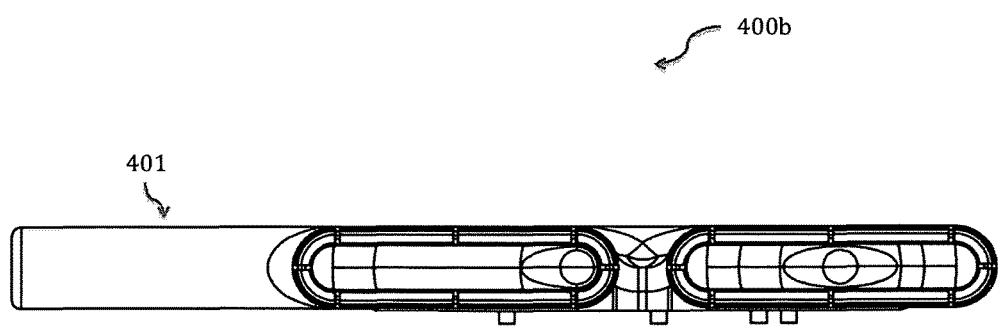
Figure 5D:
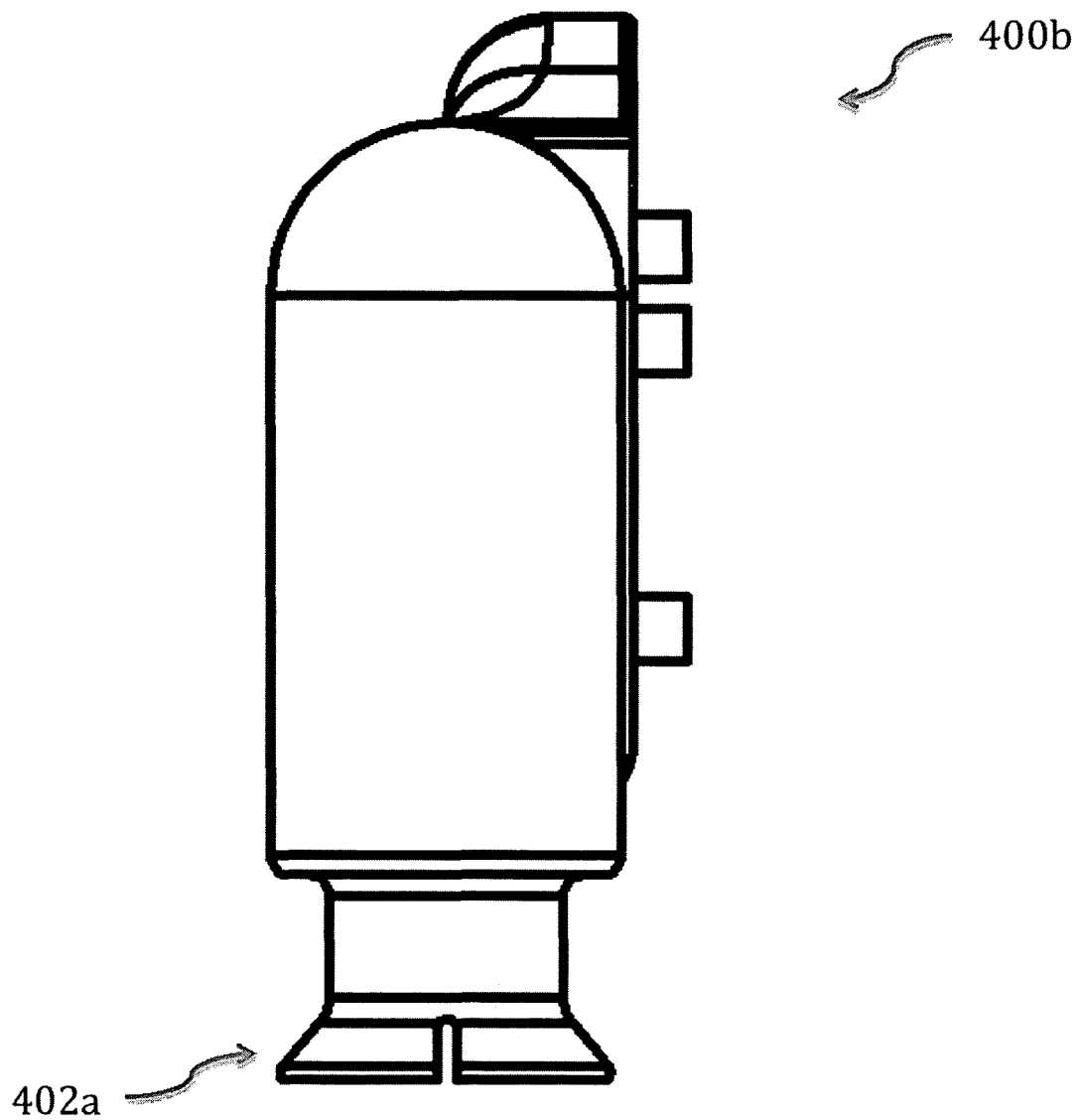
Figure 5E:
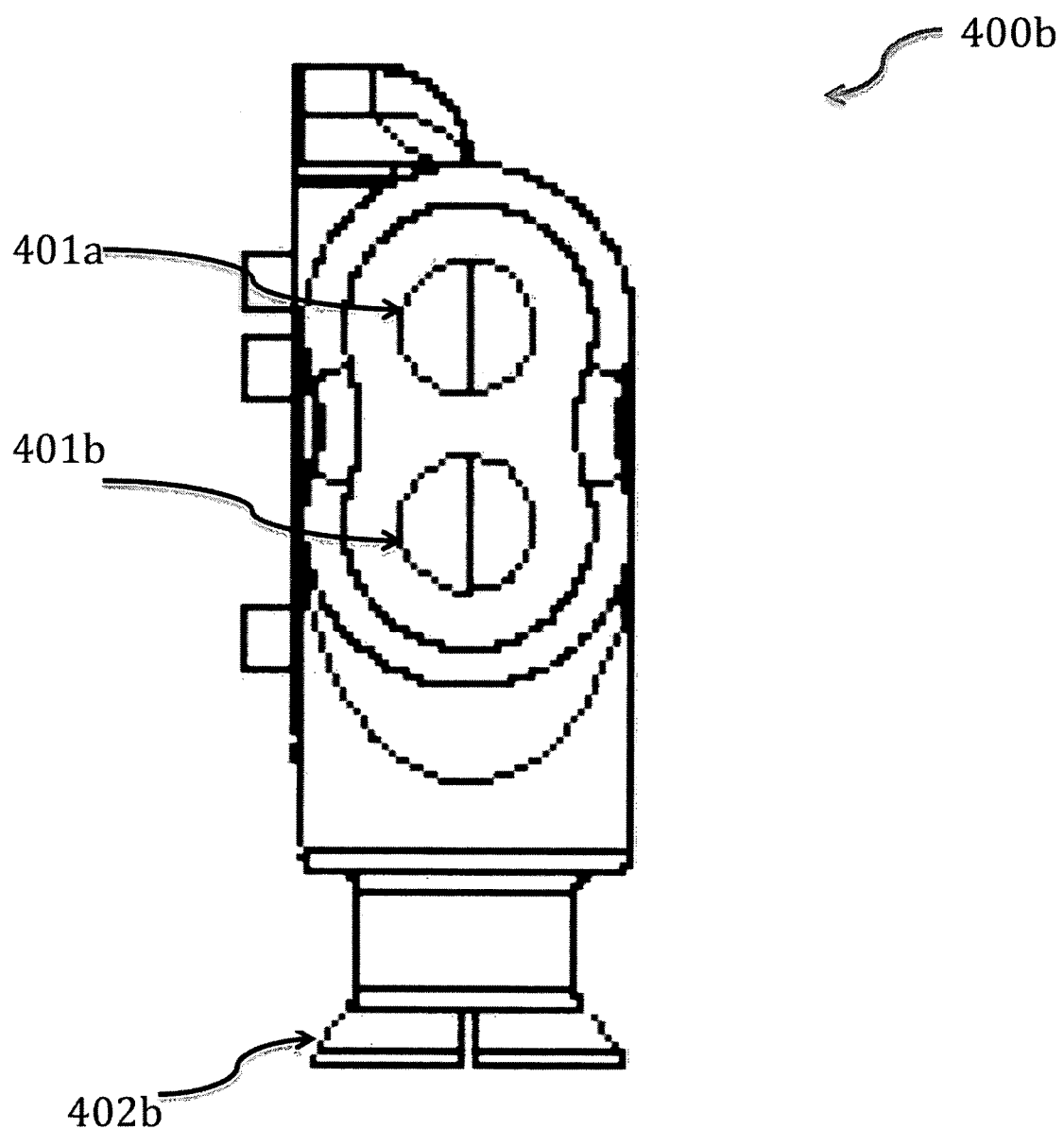
Figure 5F:
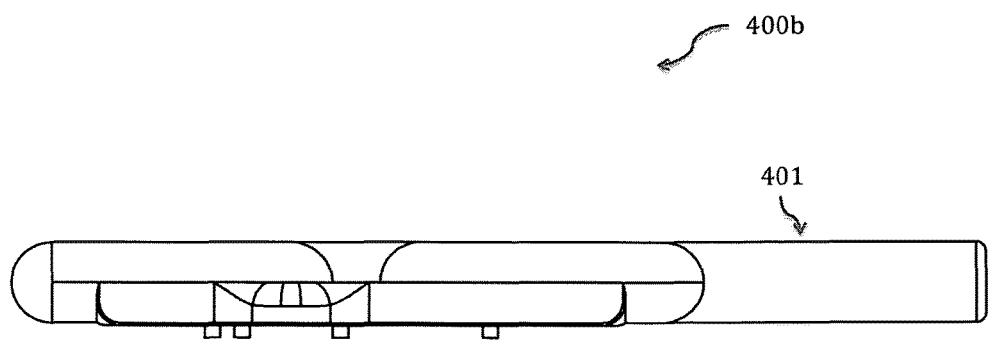
Figure 5G:
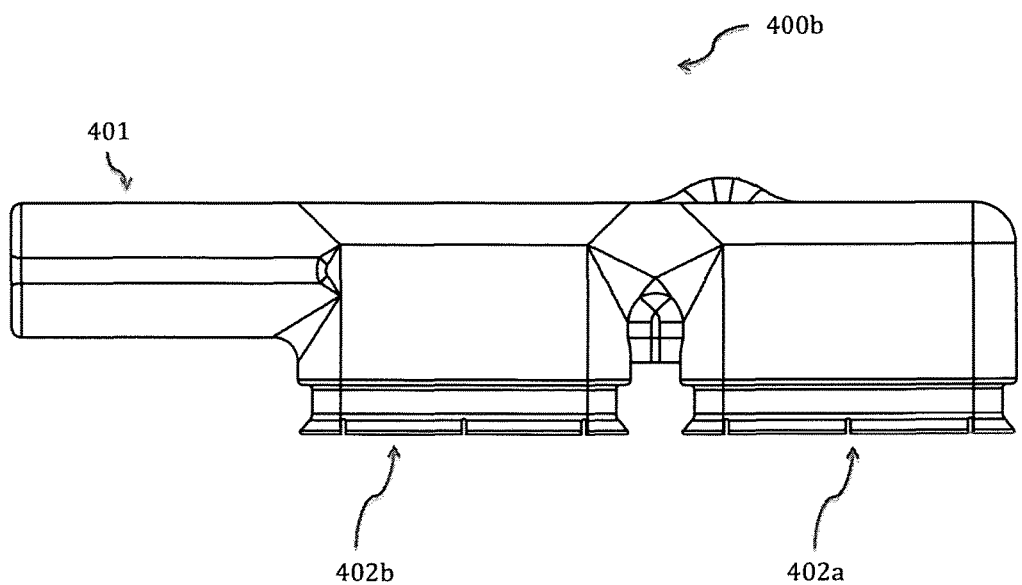
Figure 6A:
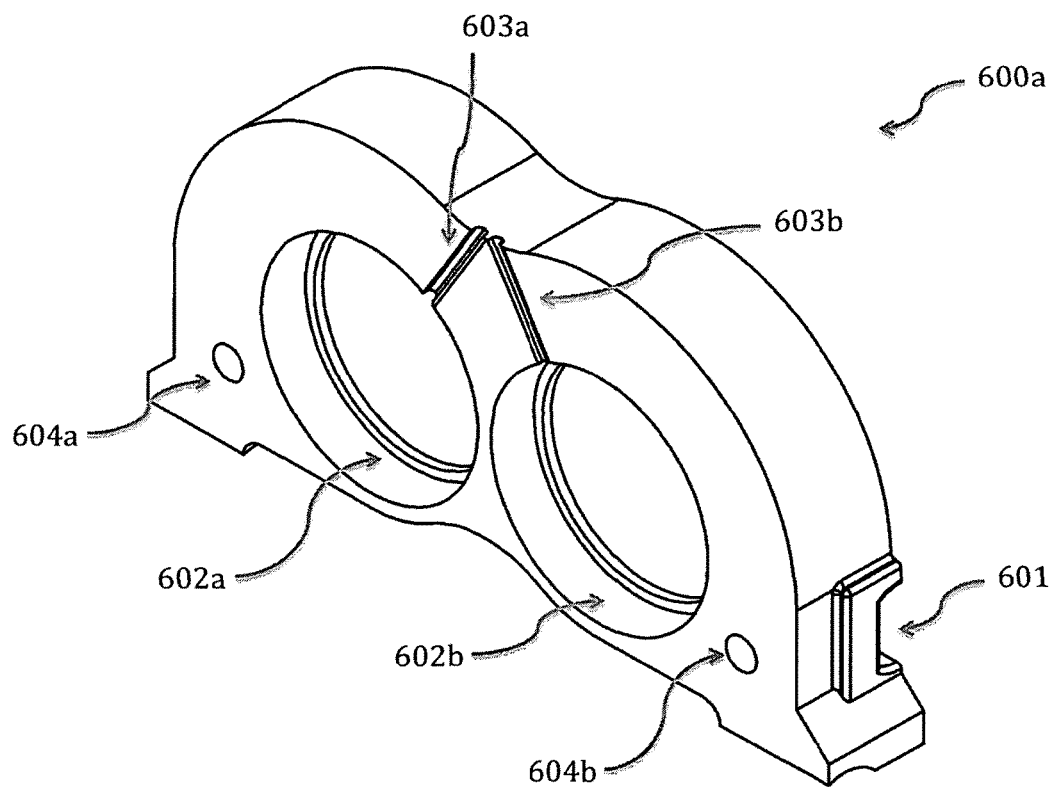
FIGS. 6A-6G illustrate the perspective, rear, top, left side, front, bottom and right side views, respectively, of a first clamshell of the cartridge system in accordance with an embodiment of the present invention.
Figure 6B:
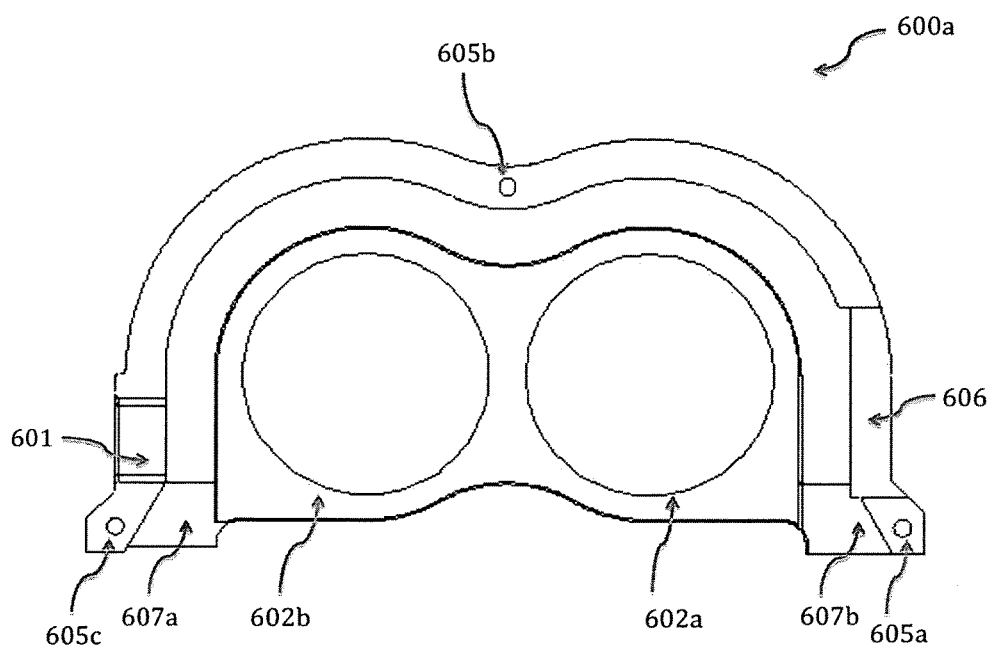
Figure 6C:
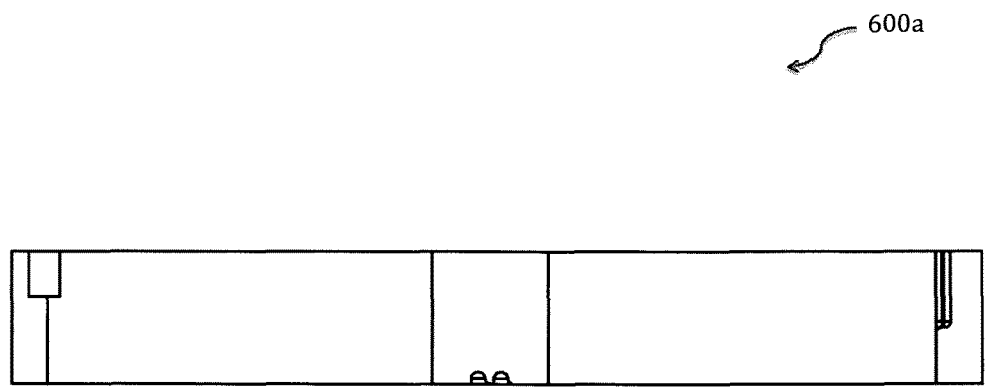
Figure 6D:
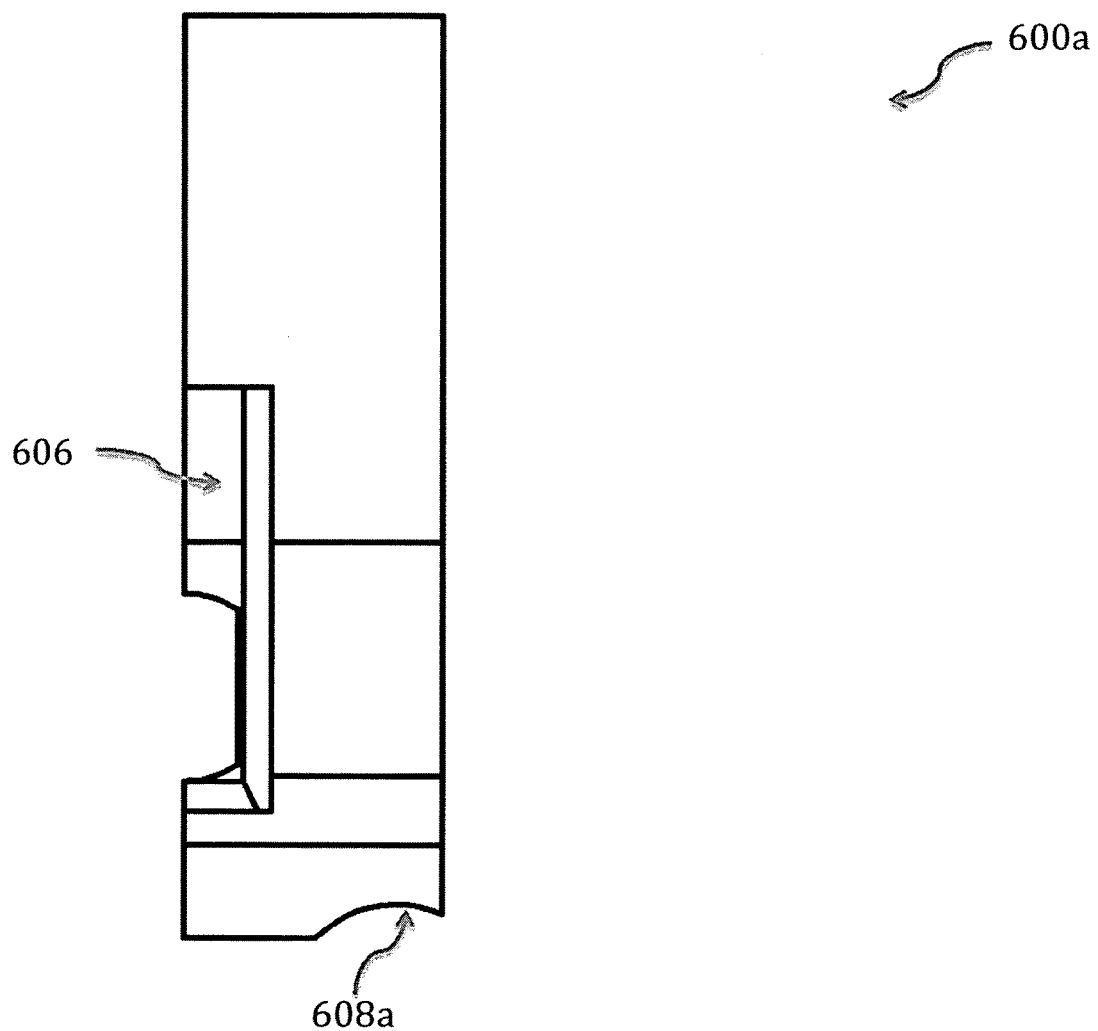
Figure 6E:
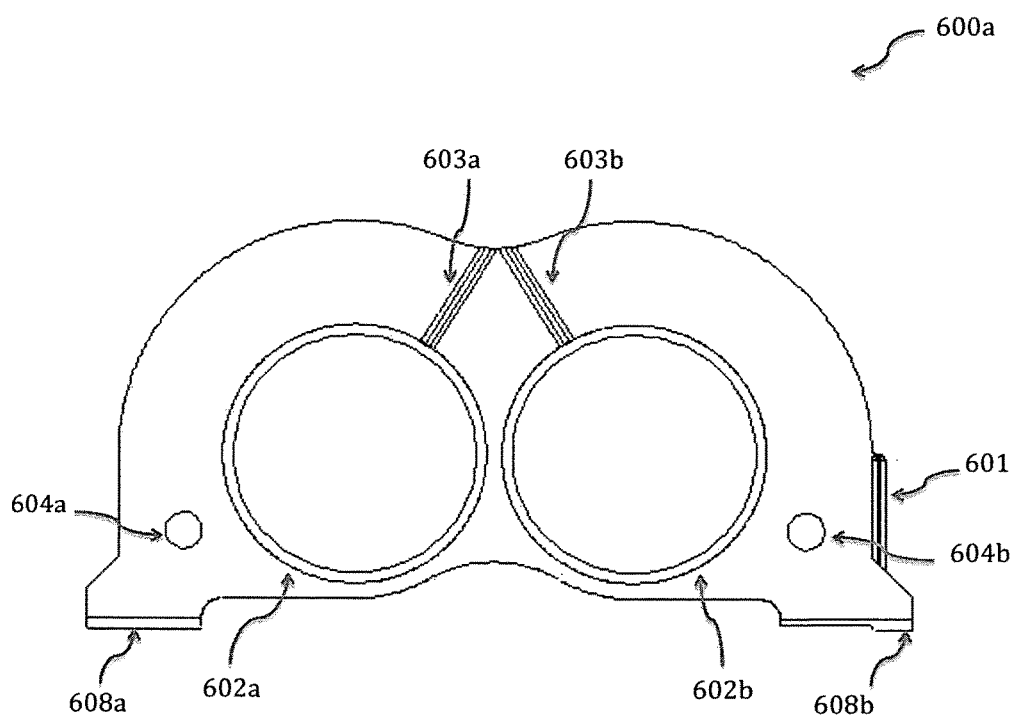
Figure 6F:
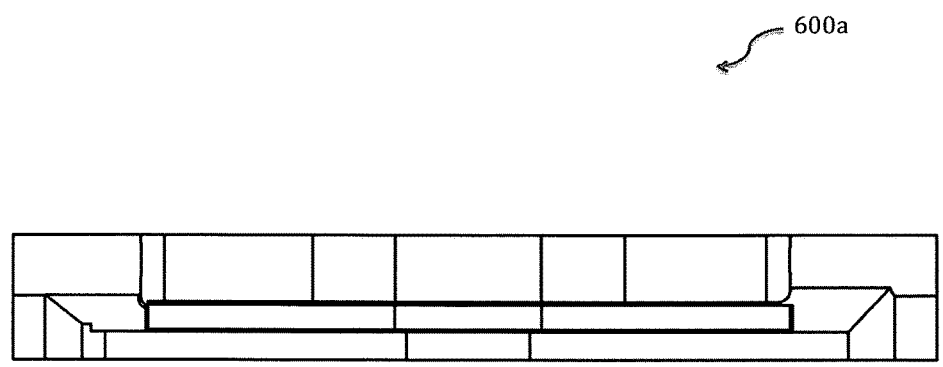
Figure 6G:
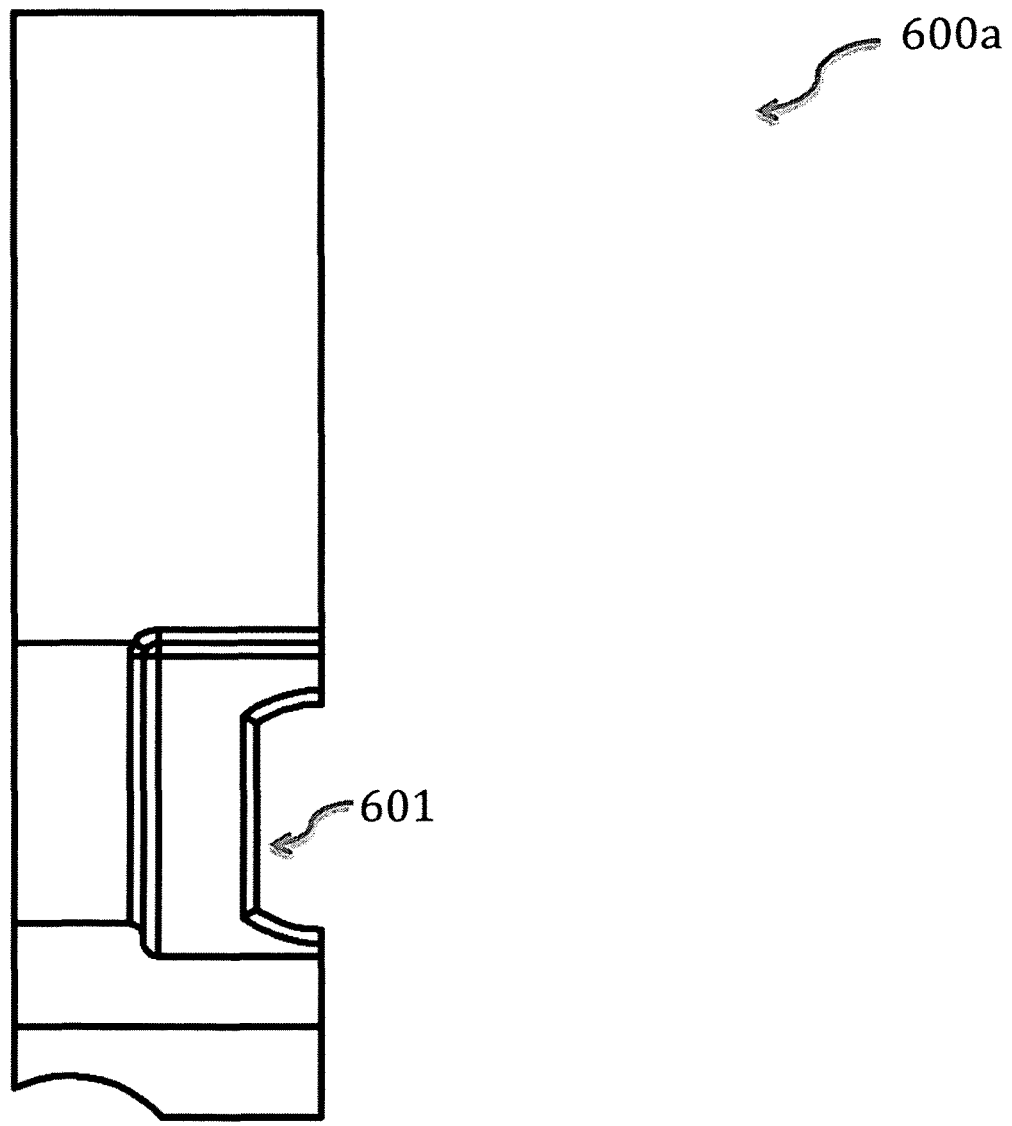
Figure 7A:
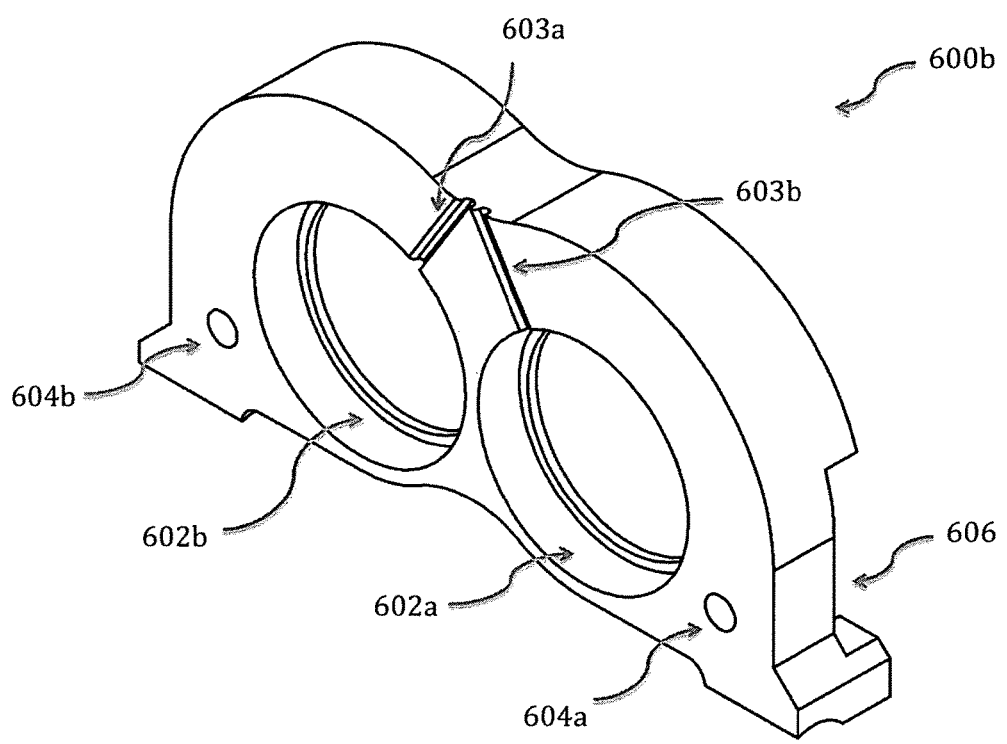
FIGS. 7A-7G illustrate the perspective, rear, left side, top, front, right side, and bottom views, respectively, of a second clamshell of the cartridge system in accordance with an embodiment of the present invention.
Figure 7B:
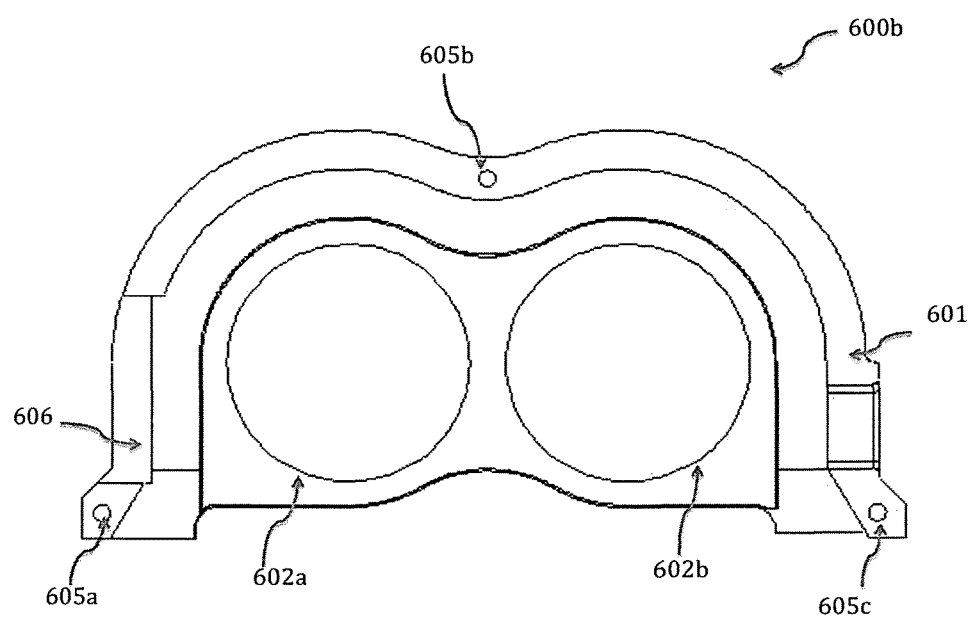
Figure 7C:
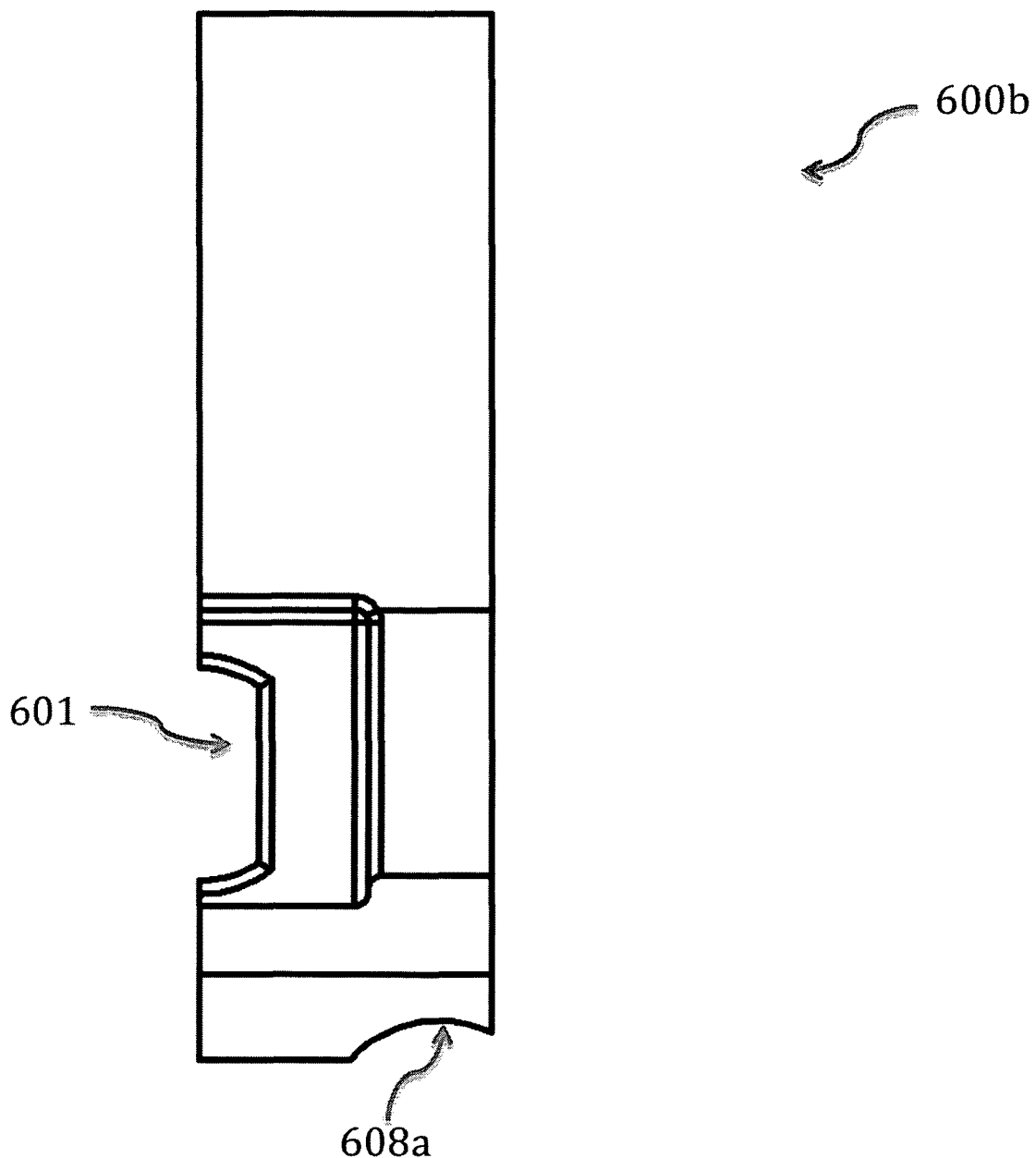
Figure 7D:
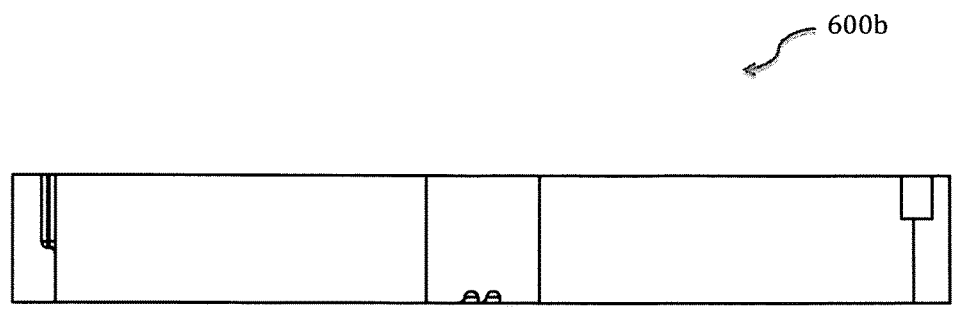
Figure 7E:
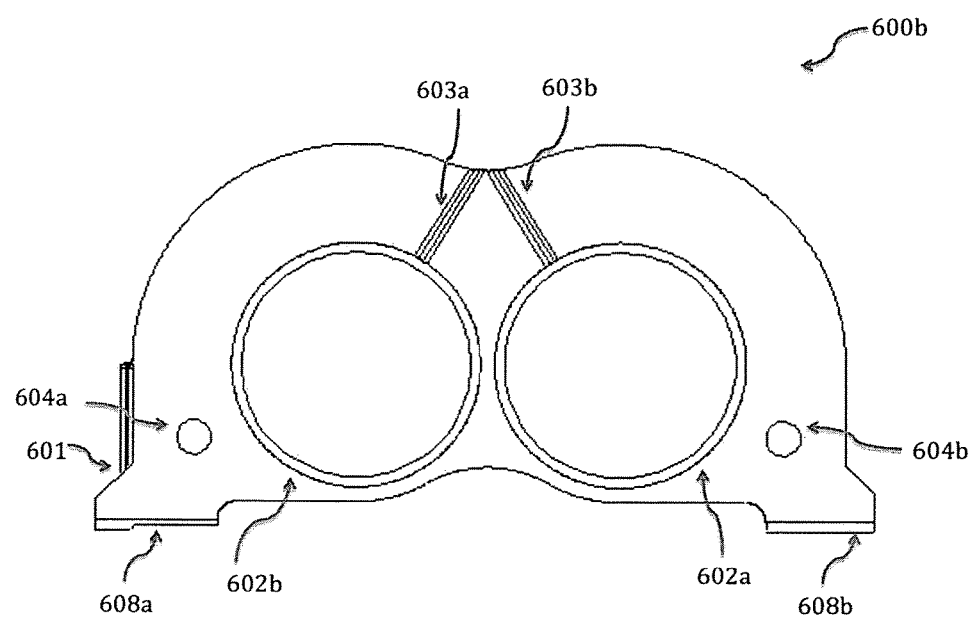
Figure 7F:
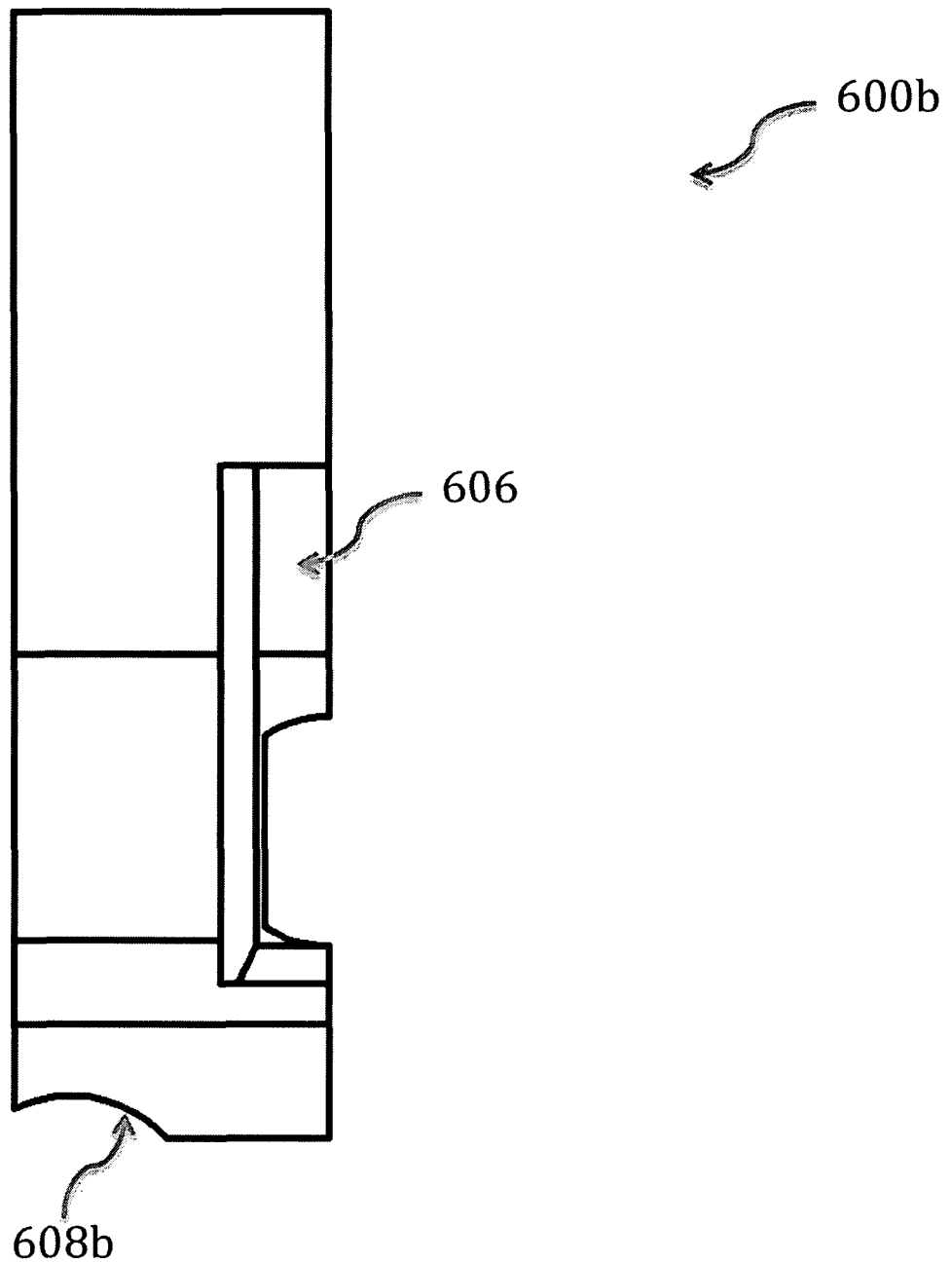
Figure 7G:
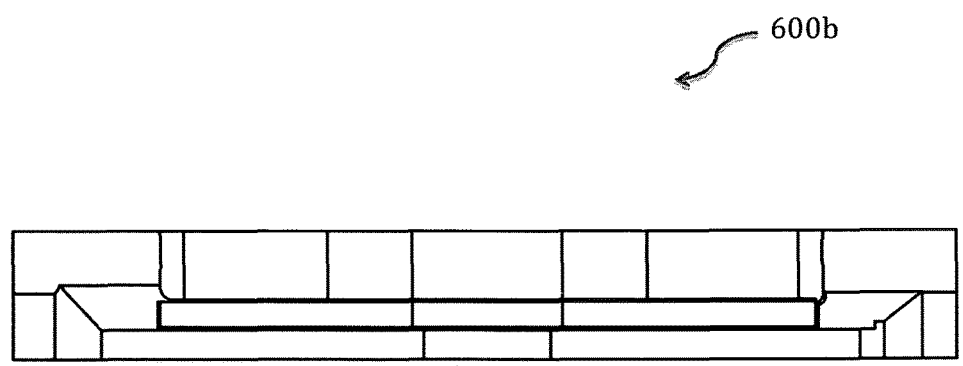
Figure 7H:
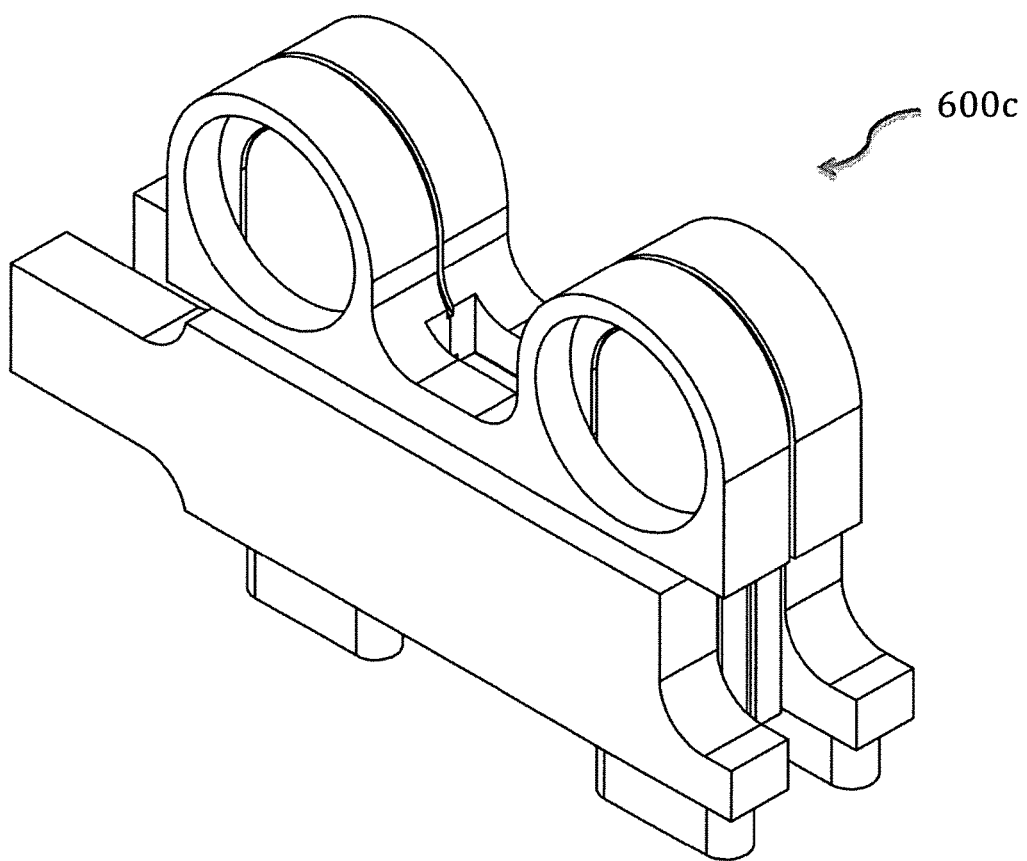
FIG. 7H illustrates a perspective view of a clamshell of the cartridge system in accordance with another embodiment of the present invention.
Figure 8A:
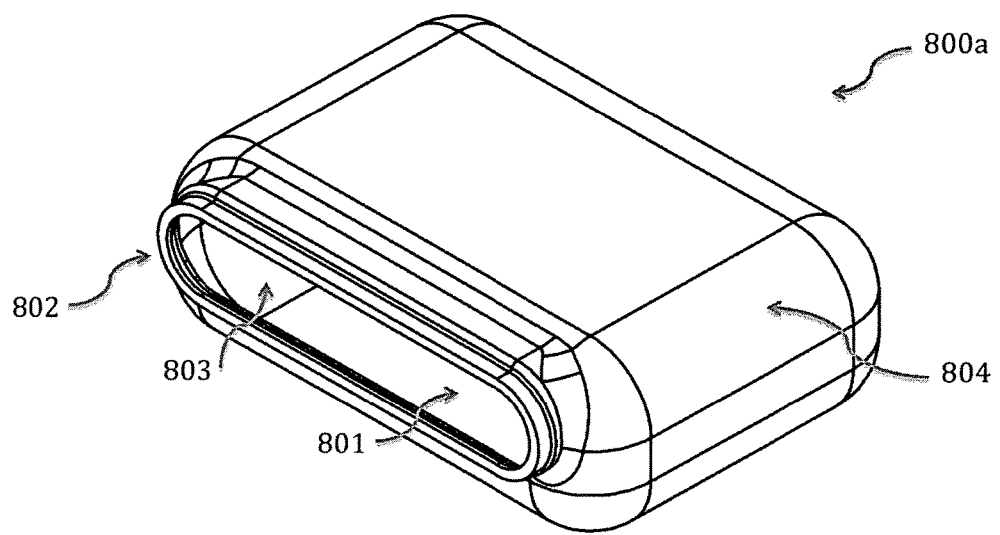
FIGS. 8A-8G illustrate the perspective, rear, top, left side, bottom, front, and right side views, respectively, of a reservoir of the cartridge system in accordance with an embodiment of the present invention.
Figure 8B:
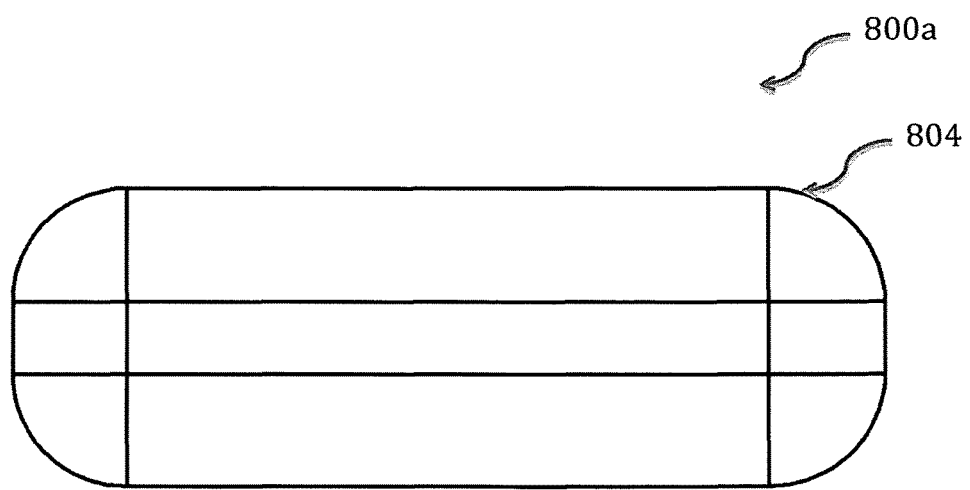
Figure 8C:
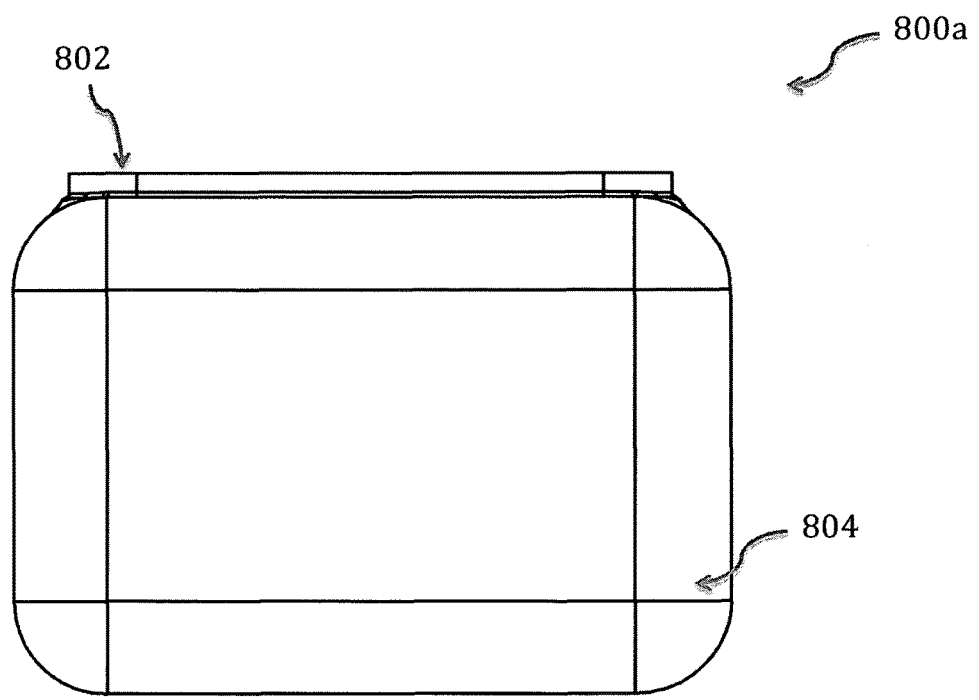
Figure 8D:
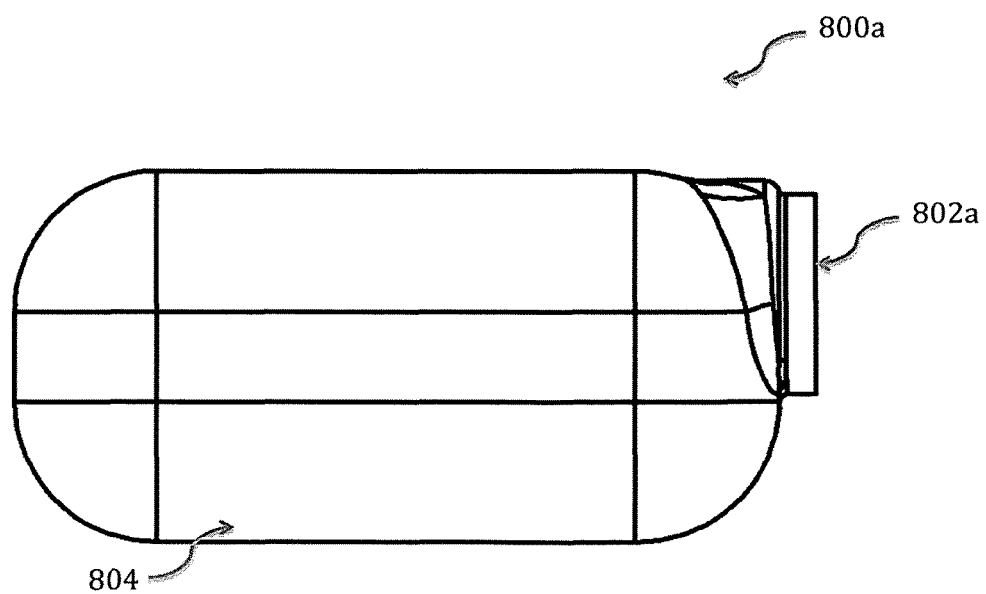
Figure 8E:
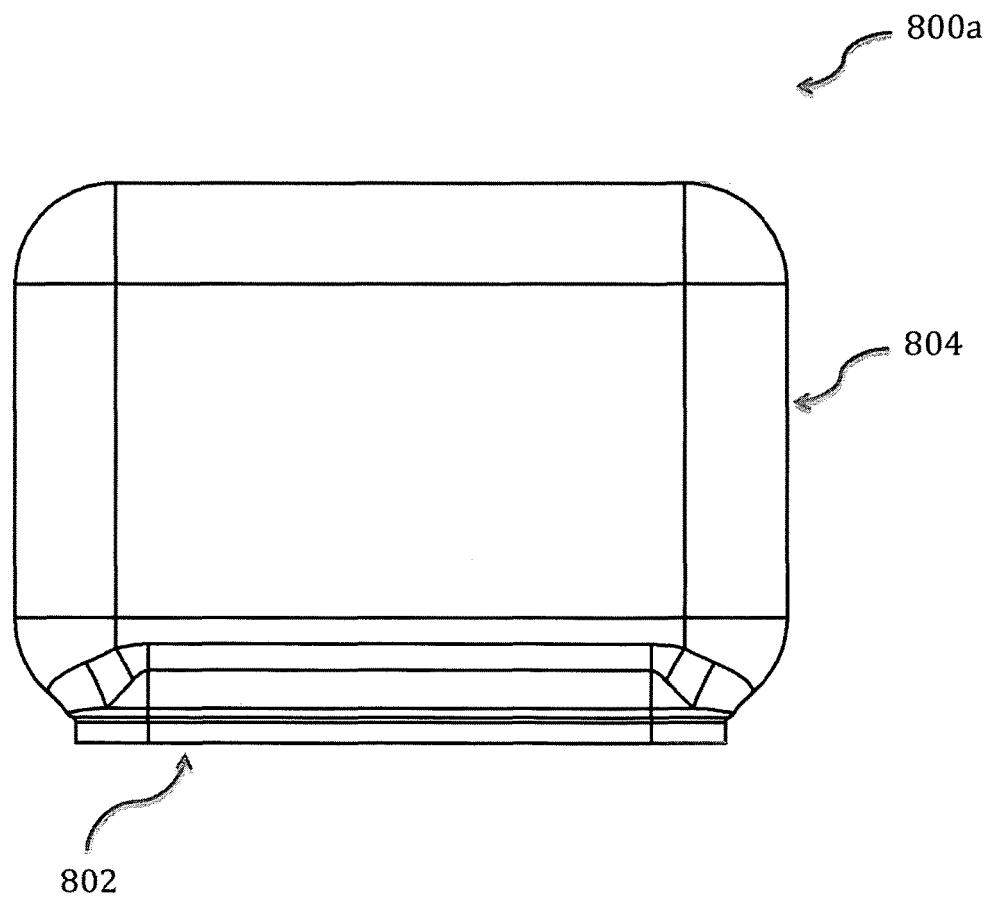
Figure 8F:
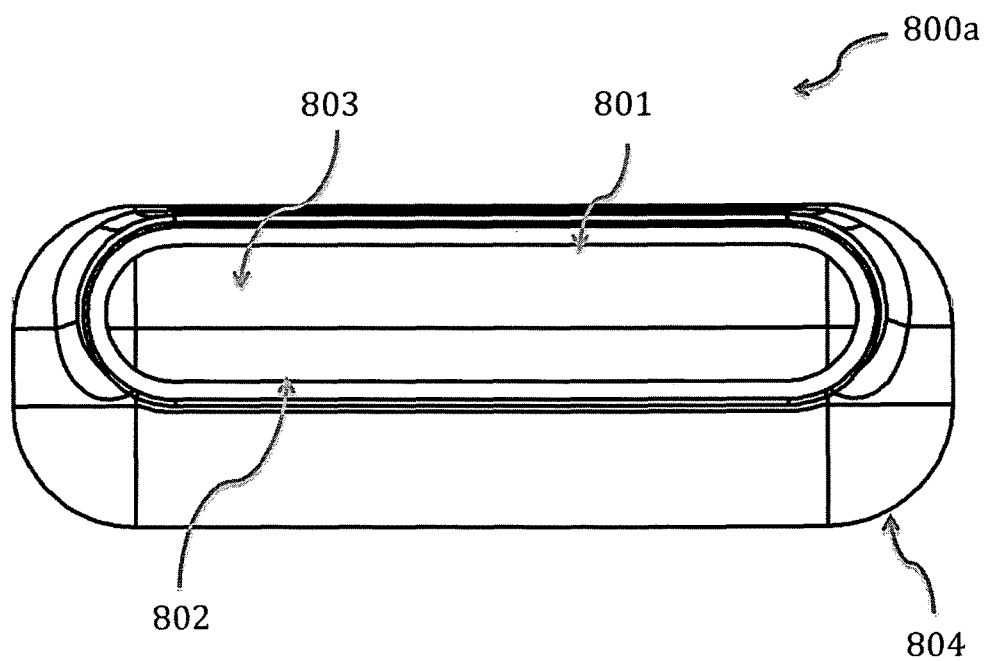
Figure 8G:
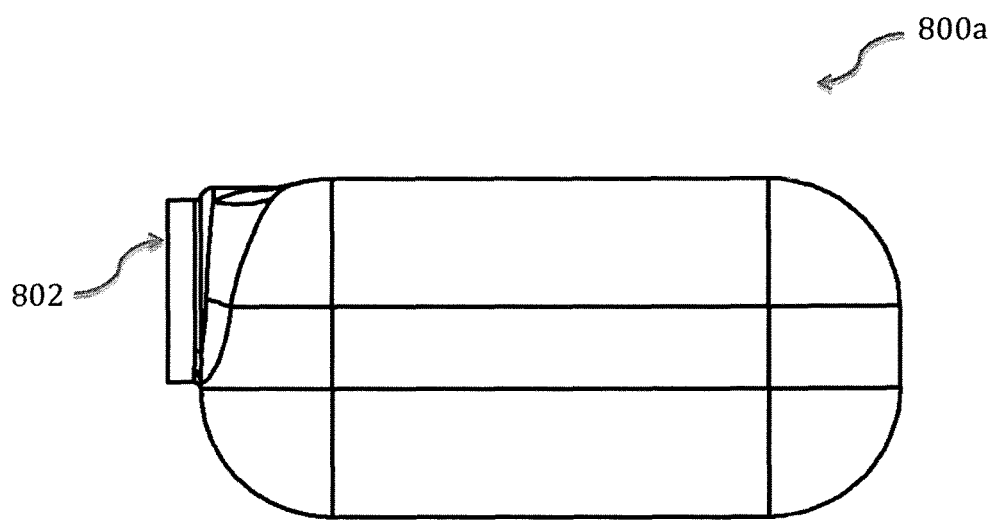

The second clamshell 600*b*, as shown in FIGS. 7A-7G, is substantially symmetrical in geometry to the first clamshell 600*a*. The clamshells 600*a*, 600*b* are preferably made of polyvinyl chloride (PVC). Referring to FIG. 7H, another embodiment of the clamshell 600*c* is shown that may be easily machineable.

Four valve membranes 700 (FIG. 12) preferably made of Silastic Q7-4840, are placed between (i) the fluid discharge openings 201*a*, 201*b* of the first and second pump body inserts 200*a*, 200*b* and the fluid receiving openings 404*a*, 404*b* of the first and second inlet/outlet members 400*a*, 400*b*, and (ii) the fluid receiving openings 202*a*, 202*b* of the first and second pump body inserts 200*a*, 200*b* and the fluid discharge openings 403*a*, 403*b* of the first and second inlet/outlet members 400*a*, 400*b*. The introduction of the valve membranes 700 (FIG. 12) within the fluid receiving and discharge openings produce passive, one-way valves which direct fluid flow within the cartridge system 100.

Referring to FIGS. 8A-8G, a reservoir 800*a* having an opening 801 is shown. The reservoir 800*a* is preferably made of elastomers and preferably made by liquid injection molding of Silastic Q7-4840 or transfer molding of Medical Grade Polyisoprene. The polymer reservoirs allow better use of the interior volume available within the pump body, and the collapsible nature of the material allows for more innovative methods for withdrawing the liquid contents.

The reservoir 800*a* has a substantially symmetrical body having a top end (not shown), a bottom end (not shown), and inner wall 803, and an outer wall 804. The top end of the reservoir 800*a* has an opening 801 that is encircled by the inner wall 803 and the outer wall 804. At the top end, the inner wall 803 and outer wall 804 project in an upward direction to form a female part 802. The female part 802 is preferably of length about 0.42 inches. The female part 802 is securely engaged to a male part 402*a*, 402*b* of a first inlet/outlet member 400*a*, or a second inlet/outlet member 400*b*.

The thickness of the reservoir 800*a* is preferably between $50\mu$ and $200\mu$. The top end, bottom end, inner wall 803, and outer wall 804 enclose a reservoir space for storage of fluid medicament. The reservoirs 800*a*, 800*b*, 800*c*, 800*d* of the cartridge system 100 are preferably quad reservoir, pre-filled with fluid medicaments, each of the reservoirs 800*a*, 800*b*, 800*c*, 800*d* capable of holding 1.5 mL of fluid medicament. Although FIGS. 8A-8G illustrate reservoir 800*a*, it must be understood that reservoirs 800*b*, 800*c*, 800*d* are substantially the same.

In another preferred embodiment of the invention, the reservoirs 800*a*, 800*b*, 800*c*, 800*d* can be replaced with two larger reservoirs 902 (FIG. 9A), of which material remains the same and the overall width is substantially doubled. The larger reservoirs 902 (FIG. 9A) of the cartridge system 902*a* (not shown) are preferably each capable of holding 3 mL of fluid medicament.

In another preferred embodiment of the invention, the reservoirs 800a, 800b, 800c, 800d can be any free-form shaped body. The reservoirs 800a, 800b, 800c, 800d can be mounted within a reservoir shell (not shown), the inside of the reservoir shell (not shown) having an insulation and sealed layer (not shown).

When the cartridge system 100 is assembled together, the first reservoir 800a, the fluid discharge opening 403a of the first inlet/outlet member 400a, the fluid receiving opening 202a of the first pump insert body 200a, the plurality of inlet channels 209a, 209b of the first pump insert body 200a, and the plurality of outlet channels 208a of the first pump insert body 200a, the fluid discharge opening 201a of the first pump insert body 200a, and the fluid receiving opening 404a of the first inlet/outlet member 400a are in fluid communication. Likewise, the second reservoir 800b, the fluid discharge opening 403b of the first inlet/outlet member 400a, the fluid receiving opening 202b of the first pump insert body 200a, the plurality of inlet channels 207a, 207b of the first pump insert body 200a, and the plurality of outlet channels 206a of the first pump insert body 200a, the fluid discharge opening 201b of the first pump insert body 200a, and the fluid receiving opening 404b of the first inlet/outlet member 400a are in fluid communication. Likewise the third reservoir 800c, the fluid discharge opening 403b of the second inlet/outlet member 400b, the fluid receiving opening 202b of the second pump insert body 200b, the plurality of inlet channels 207c of the second pump insert body 200b, and the plurality of outlet channels 206b, 206c of the second pump insert body 200b, the fluid discharge opening 201b of the second pump insert body 200b, and the fluid receiving opening 404b of the second inlet/outlet member 400b are in fluid communication. Likewise the fourth reservoir 800d, the fluid discharge opening 403a of the second inlet/outlet member 400b, the fluid receiving opening 202a of the second pump insert body 200b, the plurality of inlet channels 209c of the second pump insert body 200b, and the plurality of outlet channels 208b, 208c of the second pump insert body 200b, the fluid discharge opening 201a of the second pump insert body 200b, and the fluid receiving opening 404a of the second inlet/outlet member 400b are in fluid communication.

In another embodiment of the present invention, the medicaments can be filled in the reservoirs 800a, 800b, 800c, 800d of the cartridge system 100 using an instrument, for example, a syringe. The cartridge system 100 may have orifices (not shown) on the first and second inlet/outlet members 400a, 400b that are in fluid communication with reservoirs 800a, 800b, 800c, 800d, respectively.

Figure 9A:
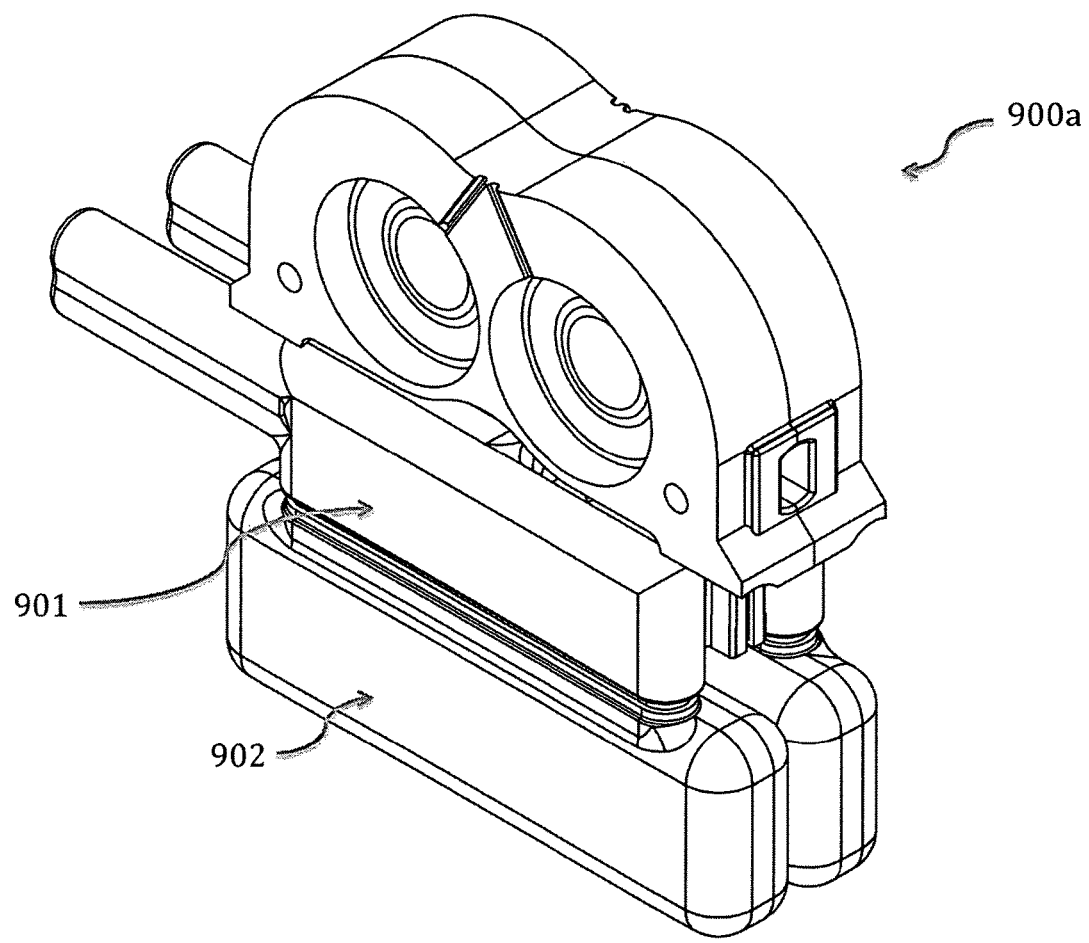
FIG. 9A illustrates a perspective view of the cartridge system in accordance with another embodiment of the present invention.
Figure 9B:
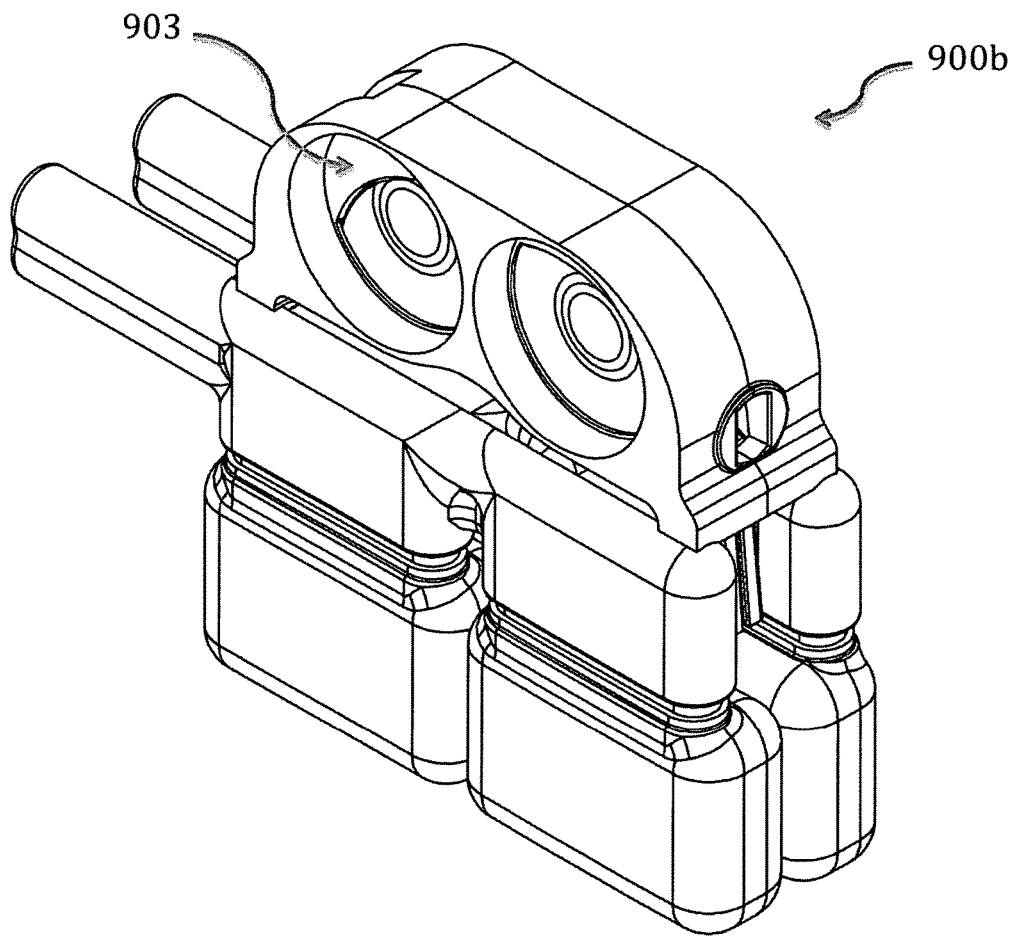
FIG. 9B illustrates a perspective view of the cartridge system in accordance with another embodiment of the present invention.

In another preferred embodiment of the present invention, as shown in FIG. 9A, the cartridge system 900a has a dual reservoir for use with two medicaments that are administered at the same rates. In yet another embodiment of the present invention, as shown in FIG. 9B, the cartridge system 900b has four reservoirs for use.

Figure 9C:
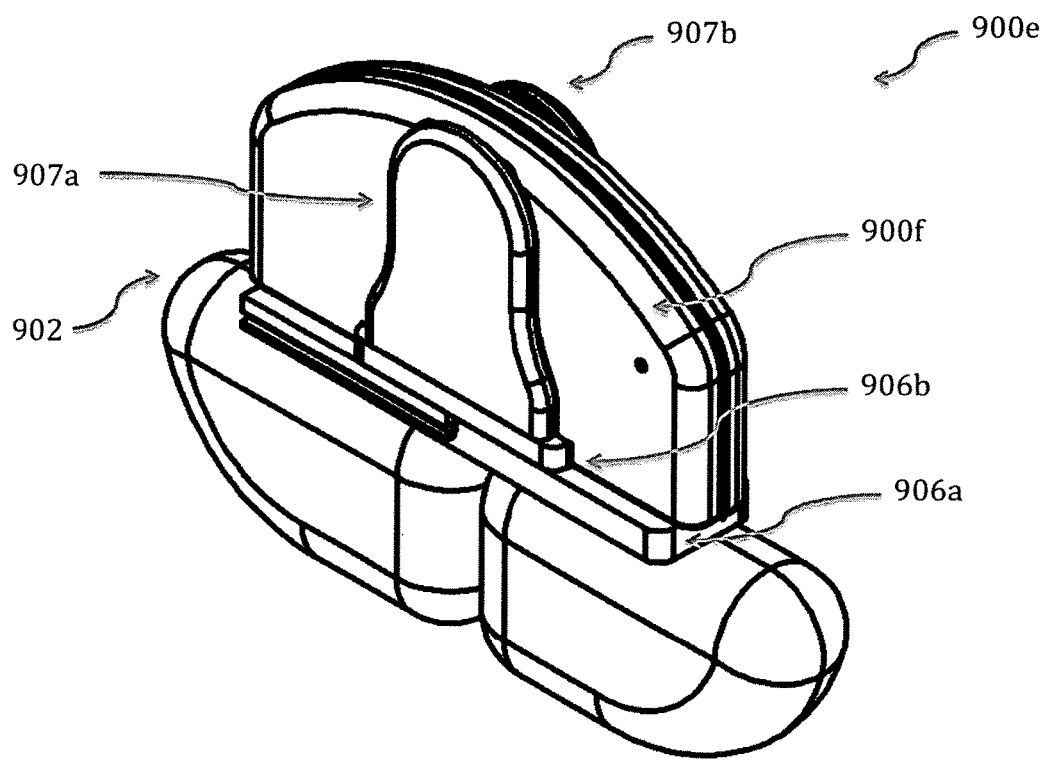
FIGS. 9C-9E illustrate a perspective view of the cartridge system, a rear view of a first pump body insert of the cartridge system, and sectional view, respectively, in accordance with another embodiment of the present invention.
Figure 9D:
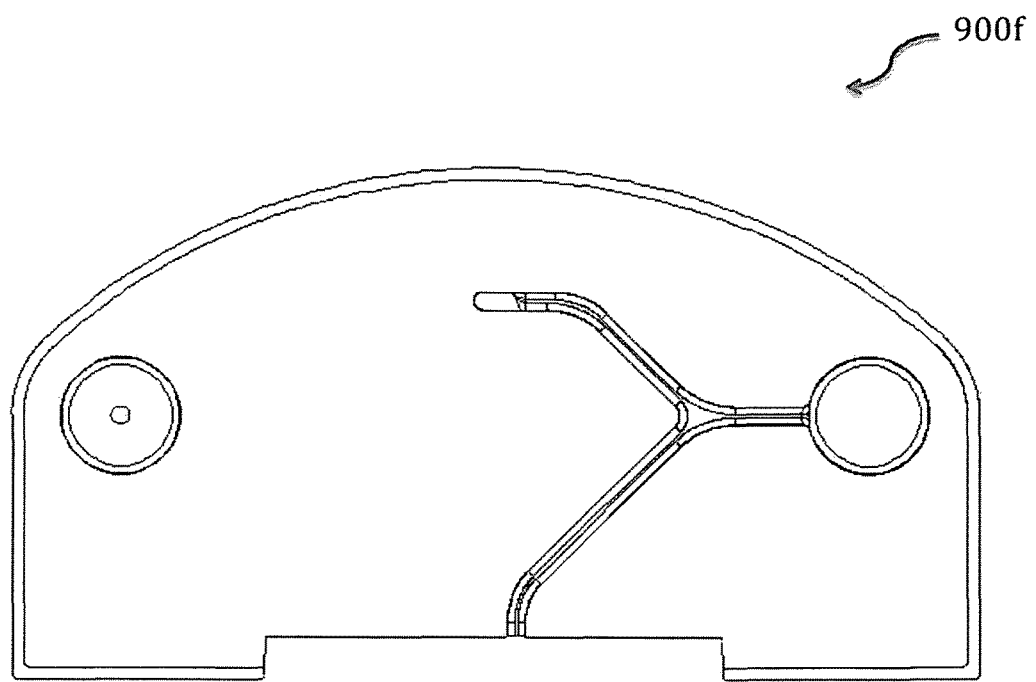

Referring to FIGS. 9C-D, another preferred embodiment of the present invention, the number of reservoirs is reduced to two for use with two medicaments rather than four. The inlet/outlet members 906a, 906b, 907a, 907b are substantially aligned to the bottom edge of the cartridge system 900e to reduce the overall thickness of the cartridge system 900e. The inlet channel 905 is in fluid communication with the inlet/outlet members 906a, 906b, 907a, 907b.

Figure 9E:
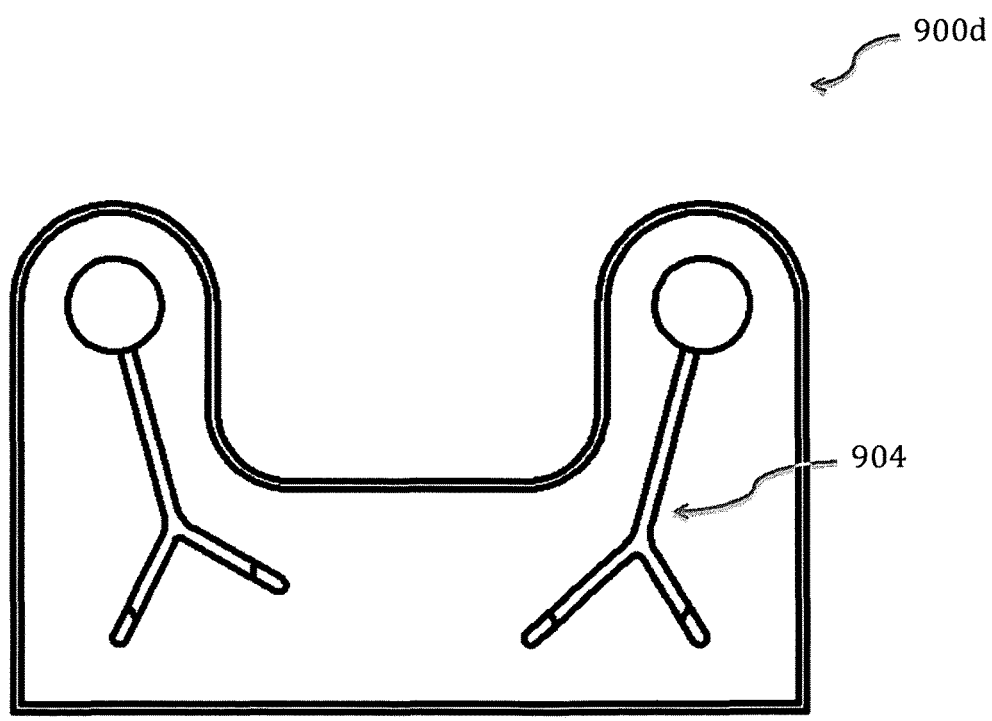

Referring to FIG. 9E, another preferred embodiment of the present invention, the overall geometry of this cartridge system, a cross-section portion of which is shown as 900d, includes features that are easy to machine. Portions of the channels 904 may be designed to be substantially straight to reduce the amount of material required for channel clearance.

In a preferred embodiment of the present invention, the multi-ported drug delivery device includes an accessory. Preferably, the accessory is an infusion set having a conduit for delivering the fluid medicament from the multi-ported drug delivery device. The conduit is preferably, a single tube catheter, a Y-catheter or a multilumen catheter. The distal end of the conduit is securely attached to a luer slip on the proximal end of the fluid outlet component 401 of the first and second inlet/outlet members 400a, 400b in the cartridge system 100. The proximal end of the conduit is securely engaged to a cannula and insertion mechanism including a sensor and a needle. When the multi-ported drug delivery device uses four reservoirs 800a, 800b, 800c, 800d, the conduit is preferably a multilumen catheter and the medicaments are mixed in the canola of the conduit before entering the needle. The mixing of the medicaments can be timed so that the medicaments will mix prior to entering the patient user's body.

In the multi-ported drug delivery device, the cartridge system 100 snaps into the pump driver system and is securely engaged to it. The pump driver system includes, among others, a driver, a controller, and a power source. The driver electromagnetically drives the magnets 300 that applies a force to the pump membrane 500 causing it to deflect resulting in precise volumetric delivery of the fluid medicament from the reservoirs 800a, 800b, 800c, 800d. This deflection of the pump membrane 500 results in a change of pressure within the chambers of the reservoirs 800a, 800b, 800c, 800d resulting in an outward flow of the fluid medicament contained within the reservoirs 800a, 800b, 800c, 800d. The magnetic force applied by the driver onto the pump membrane 500 may be adjusted using the controller and sensor(s) used to monitor the magnet movement/position. The plurality of magnets 300 and a portion of the driver are substantially axially aligned. The multi-ported drug delivery device may be powered by batteries or connected to a power outlet using an adapter, or other sources of power.

Figure 13:
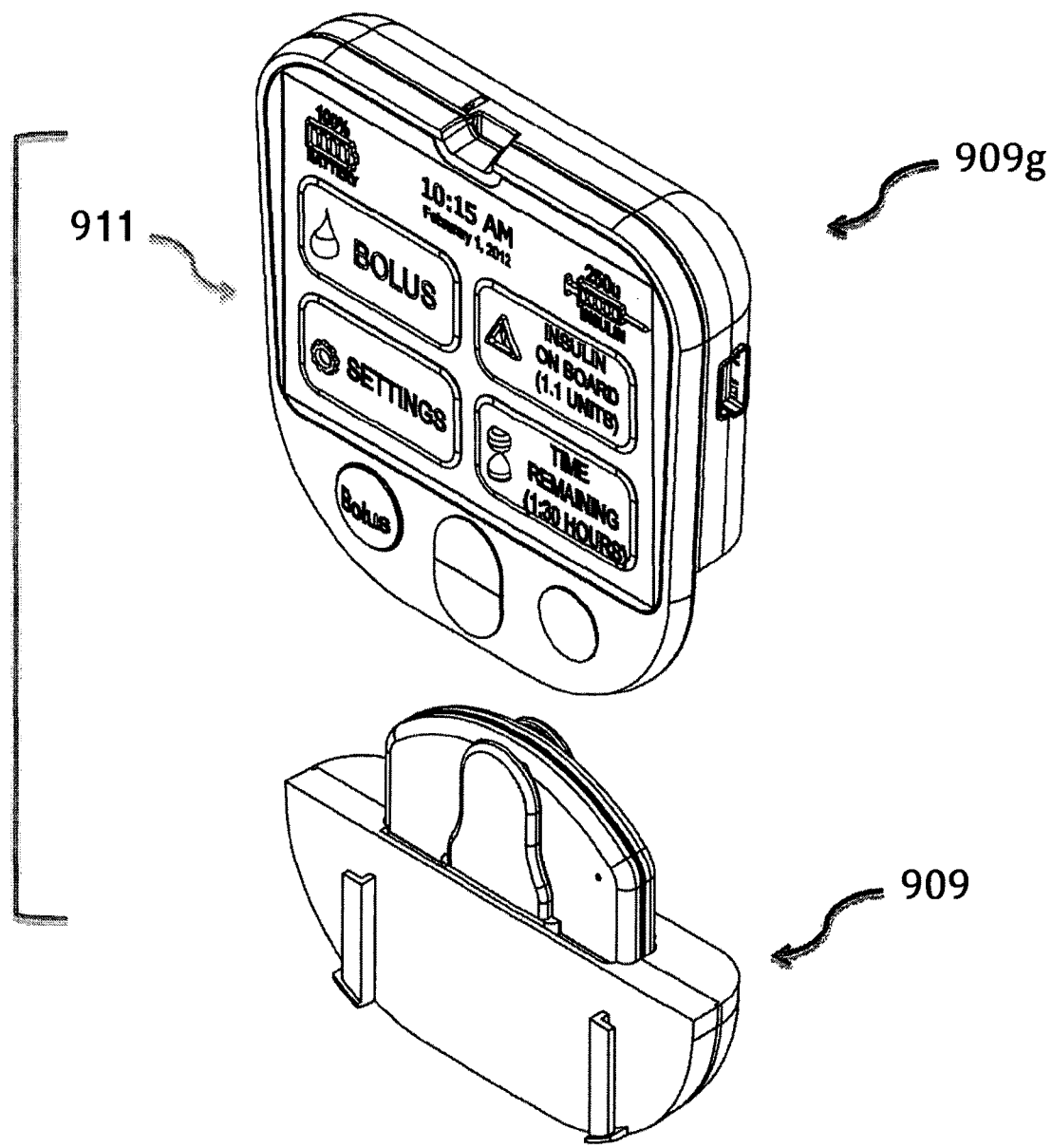
FIG. 13 illustrates a perspective view of a multi-ported drug delivery device having a cartridge system and a pump driver system in accordance with an embodiment of the present invention.

In a preferred embodiment of the present invention, the multi-ported drug delivery device includes a cartridge system 909 and a pump driver system 909 g, as shown in FIG. 13. In a preferred embodiment of the invention, a machine-readable program stored within the microcontroller of the pump driver system 909 g controls the operation of the multi-ported drug delivery device. On the device's touch screen 911, "Home" screen is the screen that will be displayed most often to the user and displays various information—time and date, medicament level in the reservoir(s), battery level, graphs of user selectable recorded data, main menu, alerts/alarms, and notifications. The patient user can access the "Main Menu" and thereby access various device settings and options. The controller runs the various checks and updates at regular intervals, for example, once per second and higher priority interrupts take precedence over checks and updates. The multi-ported drug delivery device can be programmed to deliver an appropriate dose of medicament determined by the patient user's physician or caregiver.

The multi-ported drug delivery device operates by electromagnetically driving the magnets 300 on the pump membrane 500 in a reciprocating motion. The pump membrane 500 is deflected by the magnetic force between the electromagnetic coils and the magnets 300 located on the pump membrane 500. As the magnets 300 and the pump membrane 500 are displaced, it results in a volumetric change within the pump chamber resulting in fluid flow. This change in volume results in an increased pressure on one side of the pump membrane 500 and a pressure reduction on the other side. The pressure fluctuations drive a set of dynamic check valves installed along the flow process flow line. The valves are positioned to be directionally opposed, resulting in net flow of the fluid. The high-pressure side of the pump membrane 500 forces the corresponding intake valve closed and drives the fluid through the forward facing outlet valve. At the same time, the low-pressure side of the pump membrane 500 forces the opposing outlet valve closed and draws fluid in through the forward facing inlet valve. When the direction of the pump membrane 500 changes, the role of each chamber is reversed.

The deflection of the pump membrane 500 is controlled by an actuator assembly (not shown) magnetically coupled to it and a sensor configured to detect the pump membrane's 500 position. This actuator assembly includes a driver adjustable by the controller that receives input from preferably three sensors, for example, Hall sensors (not shown) for spatial detection of the magnets' 300 position and preferably a single sensor if the magnets' 300 movements are linearly confined. The sensors can preferably be integrated within the pump housing 600a, 600b and oriented to only be sensitive to the radial component of the magnetic field (Br). They can preferably be positioned in an area where only the permanent magnet creates a non-negligible value of magnetic field (Br). The controller regulates the motion of the magnets 300 based on flow rate requirements selected by the patient user. The magnetic force imparted on the pump magnets 300 and therefore on the pump membrane 500 results in volumetric stroke and flow of the medicament from the multi-ported drug delivery device.

In a method of delivering medicament using a multi-ported drug delivery device, the multi-ported drug delivery device having the pump driver system and the cartridge system 100 is provided to the patient user. A plurality of pre-filled reservoirs 800a, 800b, 800c, 800d containing fluid medicaments are loaded to the cartridge system 100. The cartridge system 100 is then snapped into and securely engaged to the pump driver system. The user then selects various parameters on a user interface on the pump driver system. These parameters may include, but not be limited to, basal rate, insulin amount, bolus rate based on the calories of carbohydrates, protein, fat or fiber consumed, and the blood glucose level including the actual and target glucose levels. The user may either select pre-determined values or specify user-defined values for each of the parameters. The user connects an accessory, for example, an infusion set to the multi-ported drug delivery device.

The step of connecting an accessory, for example, an infusion set to the multi-ported drug delivery device may include connecting the distal ends of a Y-catheter or multi-lumen catheter to the luer slips of the outlet component of the inlet/outlet members. Subsequently, the patient user can place an inset of the infusion set on a body part of the patient user, attach the infusion set to the body, and switch on the multi-ported drug delivery device.

The delivery of medicaments can be at a controlled and continuous rate for a pre-determined or user-defined period of time. Alternatively, the delivery of medicament can also be at a programmable rate that is regulated by the patient. The drug delivery device can be preprogrammed to infuse medicaments at a constant basal rate or variable bolus rate over a certain period of time. The device can deliver micro-doses of medicaments—insulin, glucagon or other medication—at controlled and continuous rate for a pre-determined period of time.

In another method of delivering medicament using the multi-ported drug delivery device having the pump driver system and the cartridge system 100, the multi-ported drug delivery device is provided to the patient user. A plurality of reservoirs 800a, 800b, 800c, 800d are loaded to the cartridge system 100 and the reservoirs 800a, 800b, 800c, 800d are filled with medicaments using an instrument, for example, a syringe. The cartridge system 100 is then snapped into and securely engaged to the pump driver system. The patient user then selects various parameters on a user interface on the pump driver system including, but not be limited to, basal rate, insulin amount, bolus rate based on the calories of carbohydrates, protein, fat or fiber consumed, and the blood glucose level including the actual and target glucose levels. The patient user can either select pre-determined values or specify user-defined values for each of the parameters. The patient user connects an infusion set having accessory to the multi-ported drug delivery device. Subsequently, the patient user can attach the infusion set to the multi-ported drug delivery device, place an inset of the infusion set on a body part of the patient user and securely engage it, and switch on the multi-ported drug delivery device.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A multi-ported drug delivery device, comprising:
   a pump driver system, said pump driver system comprising a driver, a controller electrically coupled to said driver, and a power source;
   a cartridge system, said cartridge system comprising:
   a plurality of reservoirs, each of said plurality of reservoirs having a substantially symmetrical body with a top end, a bottom end, an outer wall, and an inner wall; an opening formed at said top end through which medicament is dispensed; and said inner wall and said bottom end forming a chamber for storage of said medicament;
   a plurality of inlet/outlet members, each of said plurality of inlet/outlet members being securely engaged to one of said plurality of reservoirs, each of said plurality of inlet/outlet members having a fluid receiving opening, a fluid discharge opening, and a fluid outlet component, and said fluid receiving opening being in fluid communication with a corresponding one of the plurality of reservoirs;
   a plurality of pump body inserts, each of said plurality of pump body inserts having a fluid receiving opening, a fluid discharge opening, a plurality of inlet channels, and a plurality of outlet channels, said fluid receiving opening of the pump body insert being in fluid communication with a corresponding one of the inlet channels, and said fluid discharge opening of the pump body insert being in fluid communication with a corresponding one of the outlet channels;

a pump membrane, said pump membrane being between said any two said plurality of pump body inserts; and a plurality of magnets, said plurality of magnets having a distal end, a proximal end and a cylindrical body connecting said distal and proximal ends, and said proximal end being in contact with said pump membrane and said distal end being housed within one of said pump body inserts, wherein the driver electromagnetically drives the plurality of magnets, wherein said plurality of magnets and a portion of said driver are substantially axially aligned.

2. The device of claim 1, further comprising: a plurality of clamshells, said clamshells having openings to house electromagnetic coils; and said clamshells having a sensor opening, said sensor opening housing a sensor to help control activation of said electromagnetic coils.

3. The device of claim 1, further comprising:

an infusion set, said infusion set comprising: a conduit for delivery of medicament, said conduit having a distal end, a proximal end, and a substantially cylindrical body connecting said distal and proximal ends of said conduit, wherein said distal end of said conduit is securely attached to a luer slip on a proximal end of said fluid outlet component of said inlet/outlet member, and wherein the proximal end of said conduit is securely engaged to a cannula and insertion mechanism.

4. The device of claim 1, wherein said pump driver system further comprises a touch screen, said touch screen being communicatively linked to said controller, and said touch screen being used to display and navigate menus, administer medicament, review saved data, modify user settings, or input general information to said device.

5. The device of claim 1, wherein said device is an independently actuated device, said reservoirs are collapsible reservoirs, and said portion of the driver comprises independently juxtaposed flat coils structurally spaced to conform to a cartridge dual chamber of the plurality of reservoirs.

6. The device of claim 1, wherein each of said plurality of reservoirs contains a different fluid medicament.

7. The device of claim 6, wherein said fluid medicament is from a group consisting of insulin and glucagon.

8. The device of claim 1, wherein said power source is capable of being recharged using a charging port.

9. The device of claim 1, wherein said plurality of reservoirs are pre-filled with medicaments.

\* \* \* \* \*